(12) United States Patent
Alvarez Berenguer et al.

(10) Patent No.: US 9,724,672 B2
(45) Date of Patent: Aug. 8, 2017

(54) PROCESS FOR THE PREPARATION OF AN ADDITIVE COMPRISING SUPPORTED AND DISPERSED TIO2 PARTICLES

(75) Inventors: Antonio Alvarez Berenguer, Madrid (ES); Aurora Maria Casado Barrasa, Alcobendas (ES); Antonio Esteban Cubillo, Madrid (ES); Javier Gravalos Moreno, Alcobendas (ES); Antonio Jose Sanchez Rojo, Alcobendas (ES); Julio Santaren Rome, Madrid (ES); Jose Vera Agullo, Alcobendas (ES)

(73) Assignees: Acciona Infraestructuras, S.A., Madrid (ES); Tolsa, S.A., Madrid (ES)

( * ) Notice: Subject to any disclaimer, the term of this patent is extended or adjusted under 35 U.S.C. 154(b) by 386 days.

(21) Appl. No.: 14/237,716

(22) PCT Filed: Aug. 7, 2012

(86) PCT No.: PCT/EP2012/065410
§ 371 (c)(1),
(2), (4) Date: Apr. 4, 2014

(87) PCT Pub. No.: WO2013/020972
PCT Pub. Date: Feb. 14, 2013

(65) Prior Publication Data
US 2015/0290619 A1    Oct. 15, 2015

(30) Foreign Application Priority Data

Aug. 8, 2011   (ES) .................................. 201131372

(51) Int. Cl.
*B01J 21/16*     (2006.01)
*B01J 37/30*     (2006.01)
(Continued)

(52) U.S. Cl.
CPC .............. *B01J 21/16* (2013.01); *A01N 25/00* (2013.01); *B01J 21/063* (2013.01); *B01J 35/004* (2013.01);
(Continued)

(58) Field of Classification Search
None
See application file for complete search history.

(56) References Cited

U.S. PATENT DOCUMENTS

| | | | |
|---|---|---|---|
| 6,824,606 B1 * | 11/2004 | Alvarez Berenguer | C04B 14/042 106/718 |
| 7,300,514 B2 * | 11/2007 | Bonafous | B01J 35/004 106/712 |
| 7,544,735 B2 * | 6/2009 | Cai | C09D 4/00 524/588 |

FOREIGN PATENT DOCUMENTS

DE        102007054848 A1    5/2009

OTHER PUBLICATIONS

Knapp et al, Phase distribution in titania—sepiolite catalyst supports prepared by different methods, 1997, 8(7), pp. 1641-1645.*

(Continued)

*Primary Examiner* — Melvin C Mayes
*Assistant Examiner* — Stefanie Cohen
(74) *Attorney, Agent, or Firm* — Hayes Soloway PC

(57) ABSTRACT

Process for the preparation of an additive comprising $TiO_2$ particles dispersed on a support of pseudo-layered phyllosilicate-type, comprising the dispersion in water of the support, the acid activation of the support and the high-shear dispersion of the support with the $TiO_2$ particles Use of the particles obtained by this process as additives with photocatalytic activity for water purification and disinfection, for purification of polluted gas streams and to provide materials, in particular construction materials, with self-cleaning, bio- (Continued)

cide, deodorization and/or pollution reduction properties in the presence of air and ultraviolet light.

19 Claims, 4 Drawing Sheets

(51) Int. Cl.
    *B01J 21/06*     (2006.01)
    *B01J 35/00*     (2006.01)
    *B01J 35/02*     (2006.01)
    *B01J 37/02*     (2006.01)
    *C04B 28/02*     (2006.01)
    *C04B 20/10*     (2006.01)
    *A01N 25/00*     (2006.01)
    *B01J 37/00*     (2006.01)
    *C04B 111/00*    (2006.01)
    *C04B 111/20*    (2006.01)

(52) U.S. Cl.
    CPC ......... *B01J 35/0006* (2013.01); *B01J 35/006* (2013.01); *B01J 35/023* (2013.01); *B01J 35/026* (2013.01); *B01J 37/009* (2013.01); *B01J 37/0207* (2013.01); *B01J 37/0209* (2013.01); *B01J 37/0217* (2013.01); *B01J 37/0221* (2013.01); *B01J 37/30* (2013.01); *C04B 20/1066* (2013.01); *C04B 28/02* (2013.01); *C04B 2111/00827* (2013.01); *C04B 2111/2069* (2013.01)

(56) References Cited

OTHER PUBLICATIONS

Fujishima et al, "Electrochemical Photolysis of Water at a Semiconductor Electrode", Nature, vol. 238, Jul. 7, 1972, pp. 37-38.
Hoffman et al, Environmental Applications of Semiconductor Photocatalysis, Chem. Rev. 1995, vol. 95, pp. 69-96.
Anpo, "Utilization of TiO2 Photocatalysts in Green Chemistry", Pure Appl. Chem. vol. 27, No. 7, 2000, pp. 1265-1270.
Nozawa et al, "Removal and Decomposition of Malodorants by Using Titanium Dioxide Photocatalyst Supported on Fiber Activated Carbon", Water Science and Technology, vol. 44 No. 9, 2001, pp. 127-133.
Benedix et al, "Application of Titanium Dioxide Photocatalysis to Create Self-Cleaning Building Materials", Lacer, 2000, 5, pp. 157-168.
Li et al, "Antimicrobial Nanomaterials for Water Disinfection and Microbial Control: Potential Applications and Implications", Water Research, 2008, vol. 42, pp. 4591-4602.
Diebold, "The Surface Science of Titanium Dioxide", Surface Science Reports No. 48 (2003) pp. 53-229.
Aranda et al, "Titania-Sepiolite Nanocomposites Prepared by a Surfactant Templating Colloidal Route", Clem. Mater., 2008, vol. 20, pp. 84-89.
Ugurlu et al, TiO2 Supported on Sepiolite: Preparation, structural and thermal characterization and catalytic bahaviour in photocatalytic treatment of phenol and lignin from olive mill wastewater, Chemical Engineering Journal 166, (2011) pp. 859-867.
Estaban-Cubillo et al, "On the Nature and Location of Nanoparticulate Iron Phases and Their Precursors Synthetized within a Sepiolite Matrix", J. Phys. Chem C 2008, vol. 112, pp. 2864-287.
AIPEA Newletter, Report on International Clay Conference, No. 4, 1970, pp. 3-4.
Pecharroman et al, "Monodisperse and Corrosion-Resistant Metallic Nanoparticles Embedded into Sepiolite Particles for Optical and Magnetic Applications", J. AM Ceram. So. vol. 89 [10] (2006) pp. 3043-3049.
Nieto-Suarez et al, "Self-assembled titania-silica-sepiolite based nanocomposites for water decontamination", J. Mater. Chem. (2009), vol. 19, pp. 2070-2075.
N.Frini-Srasra et al, "Determination of Acid-Base Properties of HCL Acid Activated Palygorskite by Potentiometrie Titration", 2008, No. 5, C 69-78.
Dahlstrom et al, "Liquid-Solid Operations and Equipment", McGraw-Hill Companies, Inc. 1999.
Mahir Alkan et al, "Electrokinetic properties of sepiolite suspensions in different electrolyte media", Journal of Colloid and Interface Science 281 (2005) 240-248.
Y. Kirsh et al, "Kinetic Analysis of Thermal Dehydration and Hydrolysis of MgCl2"6H20 by DTA and TG", Journal of Thermal Analysis, vol. 32 (1987) 393-408.
Yahong Lia et al, "Solubility prediction for the HCl—MgCl2—H2O system at 40°C. and solubility equilibrium constant calculation for HCl—MgCl2—7H2O at 40° C.", Computer Coupling of Phase Diagrams and Thermochemistry 30 (2006) 61-64.
M. Myriam et al, "Structural and Textural Modifications of Palygorskite and Sepiolite Under Acid Treatment", Clays and Clay Minerals, vol. 46, No. 3. 225-231, 1998.
Mine Ozdemir et al, "Dissolution Kinetics of Sepiolite in Hydrochloric Acid and Nitric Acid", Clays and Clay Minerals, vol. 52, No. 6, 714-720, 2004.
M. A. Vicente Rodriguez et al, "Acid Activation of a Spanish Sepiolite: Physicochemical Characterization, Free Silica Content and Surface Area of Products Obtained", Clay Minerals (1994) 29, 361-367.
C. Viseras et al, "Uses of clay minerals in semisolid health care and therapeutic products", Applied Clay Science 36 (2007) 37-50.
Ana Maria Bahamonde Santos, "Desarrollo De Catalizadores Monoliticos Para La Eliminacion De Oxidos De Nitrogeno", Tesis Doctoral, Universidad Complucense de Madrid Facultad de Ciencias Quimicas, Departamento de Ingenieria Quimica, Madrid 1992.

\* cited by examiner

PROCESS FOR THE PREPARATION OF AN ADDITIVE COMPRISING SUPPORTED AND DISPERSED TIO2 PARTICLES

The present invention relates to a process for the preparation of an additive comprising $TiO_2$ particles supported and dispersed on a pseudo-layered phyllosilicate as well as to its use as photocatalytic additive. Therefore, the invention could fit into the field of catalysis.

STATE OF THE ART

Since Fujishima and Honda introduced the phenomenon of water decomposition in the $TiO_2$ anode of a photochemical cell in 1972 (Nature, 1972, 238(37), 37-38), oxidative photocatalysis underwent a tremendous boom and numerous researchers and companies started to seek applications for said phenomenon. In the 1980s and in the first half of the 1990s, the main applications sought with the photocatalysis effect were waste water purification and its use in the chemical industry in heterogeneous catalysis (Chem. Rev., 1995, 95, 69-96). Particularly in the last decade, significant research efforts have been made consisting of the use of photocatalysts for other types of applications, such as the development of materials that reduce environmental pollution (Pure Appl. Chem., 2000, 72(7), 1265-1270) and odours (Water Sci Technol., 2000, 44(9), 127-133), development of materials with self-cleaning properties (Lacer, 2000, 5, 157-168) and development of materials with biocide properties (Water Research, 2008, 42, 4591-4602).

The physicochemical principle for all these applications is the same: photochemical reactions that take place on the surface of the photocatalysts in the presence of ultraviolet radiation. This phenomenon consists of a series of photo-induced redox reactions which take place on the catalysts degrading the substances absorbed. Likewise, the generation of $OH^-$ radicals resulting from the redox reactions means that the surface of these materials is superhydrophilic when hit by ultraviolet radiation.

Below, the generally accepted reaction mechanism for the degradation of pollutants by $TiO_2$ in the presence of ultraviolet radiation, oxygen and environmental humidity is detailed (Surf. Sci. Rep., 2003, 48, 53-229):

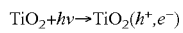

$TiO_2 + h\nu \rightarrow TiO_2(h^+, e^-)$

$TiO_2(h^+) \pm RX_{ads} \rightarrow TiO_2 RX_{ads}^{\cdot+}$

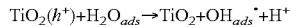

$TiO_2(h^+) + H_2O_{ads} \rightarrow TiO_2 + OH_{ads}^{\cdot} + H^+$

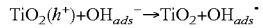

$TiO_2(h^+) + OH_{ads}^- \rightarrow TiO_2 + OH_{ads}^{\cdot}$

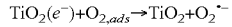

$TiO_2(e^-) + O_{2,ads} \rightarrow TiO_2 + O_2^{\cdot-}$

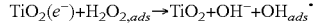

$TiO_2(e^-) + H_2O_{2,ads} \rightarrow TiO_2 + OH^- + OH_{ads}^{\cdot}$

It can be observed how, in addition to ultraviolet radiation, the presence of oxygen and water is also necessary (as source of $OH^-$ and $H^+$) for the photocatalytic process to take place. Therefore, it is necessary that the photocatalytic materials are in a medium with these three requirements for its correct activity.

Photocatalytic materials have shown themselves to be a potential solution to some of the most serious problems present in large polluted cities, both from the standpoint of reducing environmental pollution and self-cleaning surfaces, thus taking care of the aesthetic appearance.

The surfaces of the materials exposed to aggressive meteorological environments suffer degradations with the passage of time. The presence in the atmosphere of dust, physical and chemical pollutants contributes to this degradation. The conditions of humidity, rainfall and wind, among other factors, mean that these environmental pollutants reach the surface of the materials making their aesthetic appearance and durability worsen as the years pass.

Evidently, not only are the materials affected, atmospheric pollution has harmful effects that negatively affect human health. This pollution is normally generated as by-products of human activity and is mainly concentrated in large cities, which is precisely where a large part of the global population are concentrated. Therefore, a high proportion of the world population is affected by this phenomenon.

When photocatalytic materials are irradiated with ultraviolet radiation, and in the presence of water and oxygen, they catalyse the degradation of the organic and inorganic substances they come into contact with, contributing to reducing environmental pollution and to the self-cleaning of surfaces. Likewise, they also avoid the proliferation of bacteria, algae and fungi on certain surfaces, since these materials have a biocide effect partly thanks to the generation of hydroxyl radicals.

Titanium dioxide is the photocatalyst most widely used at present due to its good activity, its competitive cost and the fact that it is produced on a large scale. Furthermore, as it is a superficial effect, the activity of the photocatalyst increases when its particles have a nanometric size, since they expose more surface per unit of volume than the mass equivalent with particles of micrometric size. However, it is precisely this high surface energy that causes the agglomeration of nanoparticles due to the Van der Waals forces existing between the nanoparticles. The agglomeration of nanoparticles reduces their activity and hinders their incorporation and homogeneous dispersion when incorporated as an additive in different systems or matrices. In consequence the nanoparticles are distributed heterogeneously in the matrices they are incorporated in, and appear grouped forming large sets of nanoparticles. A solution recurrently used in catalysis is supporting the catalyst particles on a substrate. In this sense, the most widely used substrates are the metal oxides such as alumina, although there is a wide range of supports in the field of catalysis. One of the matrices used for the support of this type of nanoparticles are clays.

Some processes for obtainment of $TiO_2$ nanoparticles supported on clays have been described. Most of these processes are characterized because the $TiO_2$ is obtained "in situ" in the process by thermal treatment of the precursor supported on the clay, to obtain the corresponding oxide. Said thermal treatment affects the structural properties of the clay, (Chem. Mater., 2008, 20, 84-89, Chem. Eng. J., 2011, 166 (3), 859-867) which may affect other properties such as, for example, modifying their rheological properties. The clays used as support for obtainment of metal nanoparticles include sepiolite and attapulgite or palygorskite which, due to their structural characteristics, makes it possible to obtain homogeneous dispersions of nanoparticles, as disclosed in patent WO2005035124. Both sepiolite and attapulgite belong to the group of special clays traditionally used as absorbents for spills or in cat litter trays, or as rheological additive in construction, paints and in the animal food sector due to their high specific surface and their particular structural properties. In the case of nanoparticles, sepiolite and attapulgite have been used as support for the synthesis of nanoparticles of different nature. In this sense, obtainment processes of both metal nanoparticles of the type Ni, Ag or Cu (J. Am. Ceram. Soc. 2006, 89, 3043-3049) and oxides of the type $TiO_2$ (J. Mater. Chem., 2009, 19, 2070-2075; Chem.

Mater., 2008, 20, 84-89) or $Fe_3O_4$ (J. Phys. Chem. C 112, 2864-2871) have been described. However, the obtainment processes described to date include thermal treatments for the obtainment of nanoparticles from their precursors, with the consequent structural modification of the sepiolite or attapulgite used as support, and the loss of their rheological properties. Both the sepiolite and the attapulgite undergo structural changes as a consequence of the thermal treatment at temperatures between 350° C. and 500° C. which produces the loss of the silicate crystallization water molecules and gives rise to a collapse in the silicate structure of these clays forming the corresponding anhydrous species: anhydrous sepiolite and anhydrous attapulgite. The collapse due to thermal treatment produces the closure of the channels in the silicate structure of these clays oriented throughout the c-axis of the silicate network, and produces a reduction in the specific surface and porosity of these clays. An example of nanoparticle synthesis processes on these clays that use a thermal treatment stage is the process followed in the article described in the J. Am. Ceram. Soc. 2006, 89, 3043-3049 where different metal nanoparticles are obtained (up to 15% by weight) supported on sepiolite and protected from oxidation and perfectly dispersed. The same occurs in the case of oxides such as, for example, those of $TiO_2$ where thermal treatment is necessary for the formation of the photocatalytically active phase from the corresponding hydroxide.

Likewise, different processes have been described to support $TiO_2$ nanoparticles using both clays previously treated thermally at temperatures between 350° C. and 800° C. and untreated clays where the previously synthesized $TiO_2$ of commercial origin is dispersed on the clay in concentrations less than 5%. In this case, the clay acts as a skeleton which makes it possible to obtain an inorganic foam after a lyophilization process (J. Mater. Chem., 2009, 19, 2070-2075).

Therefore, in light of the state of the art, although the sepiolite and/or attapulgite may be suitable supports for the obtainment of homogeneously distributed $TiO_2$ nanoparticles, the processes described to date have drawbacks which limit their practical use in different applications. On the one hand, there are synthesis processes that require a thermal treatment stage for the obtainment of $TiO_2$, which alters the structure and properties of the attapulgite and sepiolite used as support. On the other hand, there are support processes on these clays of previously synthesized $TiO_2$ nanoparticles that do not require thermal treatments, but which have limitations respect to the maximum concentration of $TiO_2$ nanoparticles that it is possible to have homogeneously distributed on the clay surface. This concentration is 5% or less of $TiO_2$. Above this $TiO_2$ concentration, the $TiO_2$ nanoparticles are not deposited homogeneously and monodispersed on the clay surface but they do so forming agglomerates, which reduces their efficacy.

It would be desirable, on the one hand, to obtain higher concentrations of $TiO_2$ nanoparticles supported on the clay to enhance its photocatalytic activity in different applications such as, for example, in the construction or coatings sector, such as, for example, paints. On the other hand, it would also be desirable to not modify the structural properties and characteristics of the clay with the aim of maintaining, for example, its rheological behaviour and, in this way, achieving more homogeneous dispersions of the clay with the supported nanoparticles in the final application (for example, in loaded systems such as mortars or paints).

Furthermore, it would be convenient to maintain or increase the high absorption capacity of the natural sepiolite or attapulgite, without chemical treatment, to achieve a greater absorption of organic pollutants and other compounds that it is desirable to decompose, such as NOx, as well as a greater contact of these compounds with the $TiO_2$ nanoparticles deposited on the clay and thus manage to improve its efficacy in the photocatalytic decomposition.

The increasingly strict requirements by organizations and authorities of a cleaner environment and the need for a better quality of life means this type of photocatalytic materials with the desirable characteristics mentioned have a greater demand. Likewise, the need is arising for these materials to be increasingly active and more economical so that they can be competitive in their different applications.

DESCRIPTION OF THE INVENTION

The process described in the present invention enables resolving said problems and obtaining a high concentration of $TiO_2$ nanoparticles deposited homogeneously on sepiolite and attapulgite, without the need to use a thermal treatment stage at temperatures above 350° C. thus avoiding the alteration of the clay support and modification of its properties, in particular of the rheological properties.

Furthermore, in the product obtained by this process, the $TiO_2$ deposited on these clays, sepiolite and attapulgite, may degrade the organic pollutants in the absence of environmental humidity due to the fact that the water adsorbed on the surface of these clays is sufficient for the formation to take place of the OH radicals necessary for the decomposition of the organic compounds in the photocatalysis process mentioned above. The surface of the sepiolite and attapulgite has a very hydrophilic character as a consequence of the high density of silanol groups (—SiOH) situated throughout the edges of the silicate structure. These silanol groups may adsorb water molecules whereby it forms hydrogen bridges, and are one of the causes of the high adsorption and absorption capacity of water and other polar liquids of these clays.

The process disclosed in the present invention makes it possible to obtain a product with a high concentration of $TiO_2$ nanoparticles deposited on sepiolite where the $TiO_2$ nanoparticles are homogeneously dispersed. The percentage of $TiO_2$ nanoparticles may reach 75% without agglomeration, although from the standpoint of the cost/efficacy ratio as photocatalytic additive the percentage of $TiO_2$ is preferably in the range of 10% to 50% by weight. This product may be used in self-cleaning and pollution reduction materials since the homogeneous dispersion on sepiolite and attapulgite of the $TiO_2$ nanoparticles and the adsorption of the pollutant on the surface of these clays, allows a greater contact between them, which enhances the photocatalytic effect of decomposition as it facilitates the contact of the catalyst ($TiO_2$) and the substrate (compound to decompose). Furthermore, the reaction is not affected by relative humidity, and can be carried out in the absence of environmental humidity, as the sepiolite and attapulgite provide the water molecules adsorbed on its surface for the formation of the hydroxyl radicals necessary for the photodecomposition reaction.

The products obtained as described in the present invention can be incorporated in different materials as a photocatalytic additive to, for example, keep its aesthetic appearance unaltered during a long period of time, avoiding the proliferation of bacteria, algae and fungi and contributing to reducing many of the harmful substances responsible for atmospheric pollution, such as VOCs (volatile organic compounds), $NO_x$, $SO_x$, $NH_3$, CO, etc.

Thus, an aspect of the present invention relates to a process for the preparation of an additive, where the additive comprises $TiO_2$ particles supported and dispersed on a support, comprising the following stages:
i) the dispersion in water of the support;
ii) the acid activation of the support of stage (i); and
iii) the addition of the $TiO_2$ particles on the support of stage (ii) with high-shear mixing.

Another aspect of the present invention relates to an additive, where the additive comprises $TiO_2$ particles supported and dispersed on a support, obtainable by the process described above.

Another aspect of the present invention relates to a composition that comprises the additive described above.

Another aspect of the present invention relates to the use of the additive described above, to provide the materials, preferably construction materials, with self-cleaning, biocide, deodorization and/or pollution reduction properties in the presence of air and ultraviolet light, Another aspect of the present invention relates to the use of the additive described above, to provide the materials, preferably construction materials, with self-cleaning, biocide, deodorization and/or pollution reduction properties in the presence of air and ultraviolet light which does not require environmental humidity for its activity.

Another aspect of the present invention relates to the use of the additive described above, for water purification and disinfection.

Another aspect of the present invention relates to the use of the additive described above, for the purification of gas streams.

Another aspect of the present invention relates to the use of the additive described above for photocatalytic reactors in industrial processes.

The term "support" designates a solid material on the surface whereof the particles of a catalyst are dispersed to improve its efficacy and/or minimize its cost. The solid used as support is preferably a material with high specific surface such as, for example, a pseudo-layered phyllosilicate, in particular sepiolite or attapulgite (palygorskite).

The term "high shear" relates to conditions of reduction in size, dispersion of agglomerates and aggregates, or mixture of solids and of solids and liquids capable of applying high shear or tangential forces. These high shear forces are mainly achieved by high speed mechanical shaking systems, as well as with rotor/stator type shaking and mixing systems capable of creating a high shear velocity between the rotor and the stator. For the purposes of the present invention, high shear dispersion systems are considered to be the high speed mechanical shakers capable of developing a peripheral velocity greater than 10 m/s. Typical examples are Cowles type mixers with toothed discs. Also considered as high shear systems are the rotor/stator systems capable of developing a peripheral velocity in the rotor greater than 10 m/s and which creates a shear velocity greater than 2,000 $s^{-1}$ in the rotor/stator space. Typical examples of shakers and mixers are colloidal mills, stamping mills, toothed rotor/stator systems and Silverson-type mixers. High shear systems are also considered microball mills and two-cylinder and three-cylinder mills with cylinders rotating at different velocity and capable of generating in the space between the cylinders a velocity greater than 200 $s^{-1}$.

The term "pseudo-layered phyllosilicate", also known as "pseudo-layered silicate", relates to a phyllosilicate of type 2:1 composed of 2 two-dimensional layers of silica tetrahedrons which are joined through the apical vertex to an octahedral layer of cations, normally Mg or Mg and Al. The tetrahedral layer of silica is continuous but organized in strips with the apices of the tetrahedrons in continuous strips pointing in opposite directions. This alternation in the direction of the apical ends of the silica tetrahedrons produces discontinuities in the octrahedral layer which gives rise to channels in the silicate structure. In the case of sepiolite the octahedral cations are principally Mg and the alternation in the direction of the apical ends of the silica tetrahedrons occurs every six units. In the case of palygorskite, also known as attapulgite, the octahedral cations are fundamentally aluminium and magnesium, and the inversion of the silica tetrahedrons occurs every four units. Examples of pseudo-layered phyllosilicates or pseudo-layered silicates are sepiolite and attapulgite which are clay minerals which constitute a subdivision of this type of phyllosilicates, in accordance with the 1970 recommendation of the "AIPEA Nomenclature Committee" (AIPEA Newsletter No. 4, 3-4, 1970). Previously, these clay minerals were also known with the name of hormites.

The term "rheological properties" applied to the phyllosilicate product of the present invention ("product with rheological properties" or "rheological-grade product") relates to the capacity that this material has for substantially modifying the rheological or flow properties of the liquid systems, dispersions or pastes wherein it is introduced. These pseudo-layered phyllosilicates, due to their physicochemical characteristics and morphology, produce a structuring of the liquid phase which gives rise to an increase in the system viscosity (thickening) and/or a non-Newtonian rheological behaviour. This non-Newtonian behaviour is characterized in that the system viscosity is dependent on the shear applied to the material (pseudoplastic behaviour) and/or the time that a constant shear is applied (thixotropic behaviour). A gel force can also be generated in the system which is the force under which the suspension behaves as an elastic solid and makes it possible to maintain the dispersed particles in a stable suspension.

The term "leaching", in the present invention, relates to the dissolution of part of the cations of the structure of the solid used as support as a consequence of treatment with an acid. Especially, it relates to the dissolution of the octahedral cations, in particular aluminium and/or magnesium, of the structure of a pseudo-layered phyllosilicate, sepiolite or attapulgite.

The term "photocatalyst" or "photocatalytic" relates to a catalyst capable of generating electron-hole pairs on hitting the photons. These pairs cause new electrons to enter the conductive layer and generate OH free radicals on the photocatalyst surface in the presence of air and water. These radicals start secondary REDOX reactions capable of oxidizing volatile organic compounds (VOCs) and inorganic compounds (NOx) and decomposing them to $CO_2$, $H_2O$, $SO_2$ and $N_2$. The best known and used photocatalyst is $TiO_2$, although it is not the only one; other compounds such as ZnO, CdS, $Fe_2O_3$, Feo and ZnS can also act as photocatalysts. These photocatalysts may work directly or on a special support that facilitates/favours the process, improving the final behaviour. The most widely used supports are alumina, silicates, clays, etc.

The term "cement" relates to a hydraulic conglomerate, i.e. a finely ground inorganic material which, mixed with water forms a paste which sets and hardens by means of reactions and hydration processes and which, once hardened, conserves its resistance and stability even under the water. They are basically formed by mixtures of lime, clay and plaster, although they may contain other additions such as natural pozzolanas, blast furnace slag, lime, silica fume, fly ash, etc. Standard UNE-EN 197 includes practically all types of cement.

The term "mortar or concrete (of cement)" relates to the mixture of a type of cement with sand or gravel of different granulometries. The sand and the gravel act as volume stabilizing components, act as filling and considerably decrease the retraction. Other additives may be necessary for the correct design of the mortar and the concrete, as water reducers, aerating agents, etc. . . . . .

The term "lime mortar" relates to a mixture of lime (calcium oxide), sand and water, and can be mixed by hand (due to the fact that it is a very traditional material) or in mixing machines. The setting and hardening process varies according to whether aerated lime or hydraulic lime is used. The aerated lime is mainly composed of calcium oxide or hydroxide and undergoes a slow hardening in contact with air due to action of the atmospheric $CO_2$. The aerated lime must meet a quality criterion that adjusts to European legislation UNE-EN 459. The hydraulic lime is obtained by calcinations of a mixture of calcite and clay minerals. In the hydraulic mortar lime, in the first days after the placing on site only the excess free lime transforms into calcium carbonate. The remainder reacts forming calcium hydrosilicate or CSH gel, responsible for the greatest resistance obtained in the hydraulic lime. Sand is the volume stabilizing component, acts as filling and considerably decreases the retraction.

The term "plaster" relates to a construction material prepared from a natural rock called gypsum (calcium sulphate dihydrate: $CaSO_4.2H_2O$), by dehydration, whereto certain additions of other chemical substances can be added in the factory to modify their setting, resistance, adherence, water retention and density characteristics, which, once mixed with water, can be directly used. It is also used for the production of prefabricated materials. The plaster, as industrial product, is calcium sulphate hemihydrate ($CaSO_4.\frac{1}{2}H_2O$), also commonly called "plaster of Paris". 3 different types of plaster can be differentiated in construction: black, white and red. Black plaster is a material widely used in construction, it contains more impurities than white plaster, it is grey-coloured and with it a first layer of plaster is placed on the inside walls of buildings. White plaster is a material widely used in construction, it contains few impurities, less than black plaster, is of white colour, and with it the last layer of plaster or "finish layer" is placed on buildings' walls. Red plaster is a material highly regarded in restoration, it contains few impurities, less than black plaster, is of reddish colour, and with it the last layer of plaster or "finish layer" is placed on faces of buildings.

The term "paint" relates to a fluid product which, applied on a surface in relatively thin layers, transforms over time into a solid film which adheres to said surface, so that it coats, protects and decorates the element whereon it has been applied. There are many different types of paints, some water-based, others solvent-based and others oil-based. They usually contain a series of additions, among which $CaCO_3$ and the $TiO_2$ can be highlighted.

The term "sol-gel coating" relates to the development of thin films synthesized by sol-gel technology (from a solution, obtain a gel after a polymerization process). As an example of sol-gel coating we can cite, among others, those that use silicon alkoxides (tetraethylorthosilane, methyltriethoxysilane, etc.) as precursors of the reaction. These precursors, once dissolved in alcohol, are hydrolyzed in water to form their respective silanes and later undergo the condensation reaction as shown in the following reactions:

1) Hydrolysis reaction

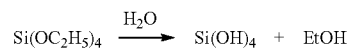

2) Condensation reaction

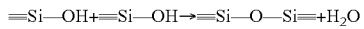

In another embodiment, the invention relates to the process described above, further comprising the following stage after stage (iii):

iv) solid/liquid separation of the support with the $TiO_2$ particles of the dispersion liquid, and later elimination of the residual water that remains in the support with the $TiO_2$ particles by drying at atmospheric pressure, at low pressure or in a vacuum.

In another embodiment, the invention relates to the process described above, where the solid/liquid separation of the support with the $TiO_2$ particles is performed by a filtration, preferably where the solid/liquid separation of the support with the $TiO_2$ particles is performed by a filtration using filtration equipment selected from press filters, pressure belt filters, vacuum belt filters, rotary vacuum filters and Nucha filters.

In another embodiment, the invention relates to the process described above, where the support is a pseudo-layered phyllosilicate.

In another embodiment, the invention relates to the process described above, where the support is essentially sepiolite.

In another embodiment, the invention relates to the process described above, where the support is essentially sepiolite and the sepiolite is rheological grade sepiolite.

In another embodiment, the invention relates to the process described above, where the support is essentially attapulgite.

In another embodiment, the invention relates to the process described above, where the support is essentially attapulgite and the attapulgite is rheological grade attapulgite.

In another embodiment, the invention relates to the process described above, where the $TiO_2$ particles that the additive is comprised of are of anatase phase, rutile phase, brookite phase or a mixture thereof.

In another embodiment, the invention relates to the process described above, where the $TiO_2$ particles that the additive is comprised of are of anatase phase.

In another embodiment, the invention relates to the process described above, where the dispersion of the support in water is adjusted to a concentration of 2 to 30% by weight.

In another embodiment, the invention relates to the process described above, where the dispersion of the support in water is adjusted to a concentration of 2% to 15% by weight.

In another embodiment, the invention relates to the process described above, where the dispersion of the support in water is performed at high shear.

In another embodiment, the invention relates to the process described above, where the dispersion of the support in water at high shear is performed with mechanical shakers where the peripheral velocity is greater than 10 m/s.

In another embodiment, the invention relates to the process described above, where the support is activated by the addition of an acid which leaches between 5% and 25% of the magnesium cations from the sepiolite structure.

In another embodiment, the invention relates to the process described above, where the support is activated by the addition of an acid which leaches between 5% and 33% of the magnesium/aluminium cations from the attapulgite structure.

In another embodiment, the invention relates to the process described above, where the acid is an organic or inorganic acid, preferably an inorganic acid of $pK_a$ less than 4.

In another embodiment, the invention relates to the process described above, where the acid is selected from hydrochloric acid, sulphuric acid, nitric acid, phosphoric acid and mixtures thereof.

In another embodiment, the invention relates to the process described above, where the resulting pH after the addition of the acid is less than 5, preferably where the resulting pH after the addition of the acid is less than or equal to 3.

In another embodiment, the invention relates to the process described above, where the acid treatment is carried out at a temperature less than 350° C.

In another embodiment, the invention relates to the process described above, where the acid treatment is carried out at a temperature between 10° C. and 100° C.

In another embodiment, the invention relates to the process described above, where the acid treatment is carried out during a time between 5 minutes and 5 hours, preferably where the acid treatment is carried out during a time between 10 minutes and 30 minutes.

In another embodiment, the invention relates to the process described above, where the $TiO_2$ particles are added to the dispersion of the support activated with acid in the form of dry powder or as a dispersion in water.

In another embodiment, the invention relates to the process described above, where, when the $TiO_2$ particles are added as a dispersion in water, the dispersion in water has a concentration of $TiO_2$ particles of between 2% and 30% by weight of $TiO_2$ particles.

In another embodiment, the invention relates to the process described above, where, when the $TiO_2$ particles are added as a dispersion in water, the dispersion in water has a concentration of $TiO_2$ particles of between 4% and 10% by weight of $TiO_2$ particles.

In another embodiment, the invention relates to the process described above, where the quantity of $TiO_2$ particles added in stage (iii) to the dispersion of the support activated with acid is adjusted so that the concentration by weight of the $TiO_2$ of the additive is between 5% and 75% by weight of $TiO_2$.

In another embodiment, the invention relates to the process described above, where the quantity of $TiO_2$ particles added in stage (iii) to the dispersion of the support activated with acid is adjusted so that the concentration by weight of the $TiO_2$ of the additive is between 15% and 50% by weight of $TiO_2$.

In another embodiment, the invention relates to the process described above, where the dispersion of the support activated with acid and the $TiO_2$ particles are subjected to an agitation and dispersion in high shear conditions during a time of between 2 and 60 minutes.

In another embodiment, the invention relates to the process described above, where the dispersion of the support activated with acid and the $TiO_2$ particles are subjected to an agitation and dispersion in high shear conditions during a time of between 5 and 20 minutes.

In another embodiment, the invention relates to the process described above, where the dispersion at high shear is performed with mechanical shakers capable of reaching a peripheral velocity equal to or greater than 10 m/s.

In another embodiment, the invention relates to the process described above, where the support has a concentration greater than 50% by weight of sepiolite and/or attapulgite.

In another embodiment, the invention relates to the process described above, where the support has a concentration greater than 85% by weight of sepiolite and/or attapulgite.

In another embodiment, the invention relates to the process described above, where the support has an average particle size less than 150 μm, preferably where the support has an average particle size less than 44 μm.

In another embodiment, the invention relates to the process described above, where the $TiO_2$ particles which are dispersed in stage (iii) have an average particle size less than 1 μm, preferably where the $TiO_2$ particles which are dispersed in stage (iii) have an average particle size less than 100 nm.

In another embodiment, the invention relates to the process described above:
where the support is essentially sepiolite, preferably where the sepiolite is rheological grade sepiolite;
where the support has a concentration greater than 85% by weight of sepiolite; and
where the support has an average particle size less than 44 μm.

In another embodiment, the invention relates to the process described above:
where the support is essentially sepiolite, preferably where the sepiolite is rheological grade sepiolite;
where the support has a concentration greater than 85% by weight of sepiolite;
where the support has an average particle size less than 44 μm; and
where the $TiO_2$ particles which are dispersed in stage (iii) have an average particle size less than 100 nm.

In another embodiment, the invention relates to the process described above:
where the support is essentially attapulgite, preferably where the attapulgite is rheological grade attapulgite;
where the support has a concentration greater than 85% by weight of attapulgite; and
where the support has an average particle size less than 44 μm.

In another embodiment, the invention relates to the process described above:
where the support is essentially attapulgite, preferably where the attapulgite is rheological grade attapulgite;
where the support has a concentration greater than 85% by weight of attapulgite;
where the support has an average particle size less than 44 μm; and
where the $TiO_2$ particles which are dispersed in stage (iii) have an average particle size less than 100 nm.

In another embodiment, the invention relates to the process described above:
further comprising the following stage after stage (iii):
iv) solid/liquid separation of the support with the $TiO_2$ particles of the dispersion liquid, and later elimination of the residual water that remains in the support with the $TiO_2$ particles by drying at atmospheric pressure, at low pressure or in a vacuum; and
where the support is essentially sepiolite, preferably where the sepiolite is rheological grade sepiolite.

In another embodiment, the invention relates to the process described above:
further comprising the following stage after stage (iii):
iv) solid/liquid separation of the support with the $TiO_2$ particles of the dispersion liquid, and later elimination of the residual water that remains in the support with the TiO$_2$ particles by drying at atmospheric pressure, at low pressure or in a vacuum; and where the support is essentially attapulgite, preferably where the attapulgite is rheological grade attapulgite.

In another embodiment, the invention relates to the process described above:
further comprising the following stage after stage (iii):
iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;
where the support is essentially sepiolite, preferably where the sepiolite is rheological grade sepiolite;
where the support has a concentration greater than 85% by weight of sepiolite; and
where the support has an average particle size less than 44 μm.

In another embodiment, the invention relates to the process described above:
further comprising the following stage after stage (iii):
iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;
where the support is essentially attapulgite, preferably where the attapulgite is rheological grade attapulgite;
where the support has a concentration greater than 85% by weight of attapulgite; and
where the support has an average particle size less than 44 μm.

In another embodiment, the invention relates to the process described above:
further comprising the following stage after stage (iii):
iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;
where the support is essentially sepiolite, preferably where the sepiolite is rheological grade sepiolite; and
where the TiO$_2$ particles that the additive is comprised of are of anatase phase.

In another embodiment, the invention relates to the process described above:
further comprising the following stage after stage (iii):
iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;
where the support is essentially attapulgite, preferably where the attapulgite is rheological grade attapulgite; and
where the TiO$_2$ particles that the additive is comprised of are of anatase phase.

In another embodiment, the invention relates to the process described above:
further comprising the following stage after stage (iii):
iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;
where the support is essentially sepiolite, preferably where the sepiolite is rheological grade sepiolite;
where the TiO$_2$ particles that the additive is comprised of are of anatase phase; and
where the dispersion of the support in water is adjusted to a concentration of 2% to 15% by weight.

In another embodiment, the invention relates to the process described above:
further comprising the following stage after stage (iii):
iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;
where the support is essentially attapulgite, preferably where the attapulgite is rheological grade attapulgite;
where the TiO$_2$ particles that the additive is comprised of are of anatase phase; and
where the dispersion of the support in water is adjusted to a concentration of 2% to 15% by weight.

In another embodiment, the invention relates to the process described above:
further comprising the following stage after stage (iii):
iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;
where the support is essentially sepiolite, preferably where the sepiolite is rheological grade sepiolite;
where the TiO$_2$ particles that the additive is comprised of are of anatase phase;
where the dispersion of the support in water is adjusted to a concentration of 2% to 15% by weight; and
where the dispersion in water is performed at high shear with mechanical shakers where the peripheral velocity is greater than 10 m/s.

In another embodiment, the invention relates to the process described above:
further comprising the following stage after stage (iii):
iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;
where the support is essentially attapulgite, preferably where the attapulgite is rheological grade attapulgite;
where the TiO$_2$ particles that the additive is comprised of are of anatase phase;
where the dispersion of the support in water is adjusted to a concentration of 2% to 15% by weight; and
where the dispersion in water is performed at high shear with mechanical shakers where the peripheral velocity is greater than 10 m/s.

In another embodiment, the invention relates to the process described above:
further comprising the following stage after stage (iii):
iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;
where the support is essentially sepiolite, preferably where the sepiolite is rheological grade sepiolite;
where the TiO$_2$ particles that the additive is comprised of are of anatase phase;
where the dispersion of the support in water is adjusted to a concentration of 2% to 15% by weight;

where the dispersion in water is performed at high shear with mechanical shakers where the peripheral velocity is greater than 10 m/s;

where the support is activated by the addition of an acid which leaches between 5% and 25% of the magnesium cations from the sepiolite structure;

where the acid is selected from hydrochloric acid, sulphuric acid, nitric acid, phosphoric acid and mixtures thereof;

where the resulting pH after the addition of the acid is less than or equal to 3;

where the acid treatment is carried out at a temperature between 10° C. and 100° C.; and where the acid treatment is carried out during a time between 10 minutes and 30 minutes.

In another embodiment, the invention relates to the process described above:

further comprising the following stage after stage (iii):

iv) solid/liquid separation of the support with the $TiO_2$ particles of the dispersion liquid, and later elimination of the residual water that remains in the support with the $TiO_2$ particles by drying at atmospheric pressure, at low pressure or in a vacuum;

where the support is essentially attapulgite, preferably where the attapulgite is rheological grade attapulgite;

where the $TiO_2$ particles that the additive is comprised of are of anatase phase;

where the dispersion of the support in water is adjusted to a concentration of 2% to 15% by weight;

where the dispersion in water is performed at high shear with mechanical shakers where the peripheral velocity is greater than 10 m/s;

where the support is activated by the addition of an acid which leaches between 5% and 33% of the magnesium/aluminium cations from the attapulgite structure;

where the acid is selected from hydrochloric acid, sulphuric acid, nitric acid, phosphoric acid and mixtures thereof;

where the resulting pH after the addition of the acid is less than or equal to 3;

where the acid treatment is carried out at a temperature between 10° C. and 100° C.; and where the acid treatment is carried out during a time between 10 minutes and 30 minutes.

In another embodiment, the invention relates to the process described above:

further comprising the following stage after stage (iii):

iv) solid/liquid separation of the support with the $TiO_2$ particles of the dispersion liquid, and later elimination of the residual water that remains in the support with the $TiO_2$ particles by drying at atmospheric pressure, at low pressure or in a vacuum;

where the support is essentially sepiolite, preferably where the sepiolite is rheological grade sepiolite;

where the $TiO_2$ particles that the additive is comprised of are of anatase phase;

where the dispersion of the support in water is adjusted to a concentration of 2% to 15% by weight;

where the dispersion in water is performed at high shear with mechanical shakers where the peripheral velocity is greater than 10 m/s;

where the support is activated by the addition of an acid which leaches between 5% and 25% of the magnesium cations from the sepiolite structure;

where the acid is selected from hydrochloric acid, sulphuric acid, nitric acid, phosphoric acid and mixtures thereof;

where the resulting pH after the addition of the acid is less than or equal to 3;

where the acid treatment is carried out at a temperature between 10° C. and 100° C.;

where the acid treatment is carried out during a time between 10 minutes and 30 minutes;

where the $TiO_2$ particles are added to the dispersion of the support activated with acid in the form of dry powder or as a dispersion in water;

where, when the $TiO_2$ particles are added as a dispersion in water, the dispersion in water has a concentration of $TiO_2$ particles of between 4% and 10% by weight of $TiO_2$ particles;

where the quantity of $TiO_2$ particles added in stage (iii) to the dispersion of the support activated with acid is adjusted so that the concentration by weight of the $TiO_2$ of the additive is between 15% and 50% by weight of $TiO_2$;

where the dispersion of the support activated with acid and the $TiO_2$ particles are subjected to an agitation and dispersion in high shear conditions during a time of between 5 and 20 minutes; and where the dispersion at high shear is performed with mechanical shakers capable of reaching a peripheral velocity equal to or greater than 10 m/s.

In another embodiment, the invention relates to the process described above:

further comprising the following stage after stage (iii):

iv) solid/liquid separation of the support with the $TiO_2$ particles of the dispersion liquid, and later elimination of the residual water that remains in the support with the $TiO_2$ particles by drying at atmospheric pressure, at low pressure or in a vacuum;

where the support is essentially attapulgite, preferably where the attapulgite is rheological grade attapulgite;

where the $TiO_2$ particles that the additive is comprised of are of anatase phase;

where the dispersion of the support in water is adjusted to a concentration of 2% to 15% by weight;

where the dispersion in water is performed at high shear with mechanical shakers where the peripheral velocity is greater than 10 m/s;

where the support is activated by the addition of an acid which leaches between 5% and 33% of the magnesium/aluminium cations from the attapulgite structure;

where the acid is selected from hydrochloric acid, sulphuric acid, nitric acid, phosphoric acid and mixtures thereof;

where the resulting pH after the addition of the acid is less than or equal to 3;

where the acid treatment is carried out at a temperature between 10° C. and 100° C.;

where the acid treatment is carried out during a time between 10 minutes and 30 minutes;

where the $TiO_2$ particles are added to the dispersion of the support activated with acid in the form of dry powder or as a dispersion in water;

where, when the $TiO_2$ particles are added as a dispersion in water, the dispersion in water has a concentration of $TiO_2$ particles of between 4% and 10% by weight of $TiO_2$ particles;

where the quantity of $TiO_2$ particles added in stage (iii) to the dispersion of the support activated with acid is adjusted so that the concentration by weight of the $TiO_2$ of the additive is between 15% and 50% by weight of $TiO_2$; 1 where the dispersion of the support activated with acid and the TiO$_2$ particles are subjected to an agitation and dispersion in high shear conditions during a time of between 5 and 20 minutes; and where the dispersion at high shear is performed with mechanical shakers capable of reaching a peripheral velocity equal to or greater than 10 m/s.

In another embodiment, the invention relates to the process described above:

further comprising the following stage after stage (iii):

iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;

where the support is essentially sepiolite, preferably where the sepiolite is rheological grade sepiolite;

where the TiO$_2$ particles that the additive is comprised of are of anatase phase;

where the dispersion of the support in water is adjusted to a concentration of 2% to 15% by weight;

where the dispersion in water is performed at high shear with mechanical shakers where the peripheral velocity is greater than 10 m/s;

where the support is activated by the addition of an acid which leaches between 5% and 25% of the magnesium cations from the sepiolite structure;

where the acid is selected from hydrochloric acid, sulphuric acid, nitric acid, phosphoric acid and mixtures thereof;

where the resulting pH after the addition of the acid is less than or equal to 3;

where the acid treatment is carried out at a temperature between 10° C. and 100° C.;

where the acid treatment is carried out during a time between 10 minutes and 30 minutes;

where the TiO$_2$ particles are added to the dispersion of the support activated with acid in the form of dry powder or as a dispersion in water;

where, when the TiO$_2$ particles are added as a dispersion in water, the dispersion in water has a concentration of TiO$_2$ particles of between 4% and 10% by weight of TiO$_2$ particles;

where the quantity of TiO$_2$ particles added in stage (iii) to the dispersion of the support activated with acid is adjusted so that the concentration by weight of the TiO$_2$ of the additive is between 15% and 50% by weight of TiO$_2$; l where the dispersion of the support activated with acid and the TiO$_2$ particles are subjected to an agitation and dispersion in high shear conditions during a time of between 5 and 20 minutes;

where the dispersion at high shear is performed with mechanical shakers capable of reaching a peripheral velocity equal to or greater than 10 m/s;

where the support has an average particle size less than 44 μm; and where the TiO$_2$ particles which are dispersed in stage (iii) have an average particle size less than 100 nm.

In another embodiment, the invention relates to the process described above:

further comprising the following stage after stage (iii):

iv) solid/liquid separation of the support with the TiO$_2$ particles of the dispersion liquid, and later elimination of the residual water that remains in the support with the TiO$_2$ particles by drying at atmospheric pressure, at low pressure or in a vacuum;

where the support is essentially attapulgite, preferably where the attapulgite is rheological grade attapulgite;

where the TiO$_2$ particles that the additive is comprised of are of anatase phase;

where the dispersion of the support in water is adjusted to a concentration of 2% to 15% by weight;

where the dispersion in water is performed at high shear with mechanical shakers where the peripheral velocity is greater than 10 m/s;

where the support is activated by the addition of an acid which leaches between 5% and 33% of the magnesium/aluminium cations from the attapulgite structure;

where the acid is selected from hydrochloric acid, sulphuric acid, nitric acid, phosphoric acid and mixtures thereof;

where the resulting pH after the addition of the acid is less than or equal to 3;

where the acid treatment is carried out at a temperature between 10° C. and 100° C.;

where the acid treatment is carried out during a time between 10 minutes and 30 minutes;

where the TiO$_2$ particles are added to the dispersion of the support activated with acid in the form of dry powder or as a dispersion in water;

where, when the TiO$_2$ particles are added as a dispersion in water, the dispersion in water has a concentration of TiO$_2$ particles of between 4% and 10% by weight of TiO$_2$ particles;

where the quantity of TiO$_2$ particles added in stage (iii) to the dispersion of the support activated with acid is adjusted so that the concentration by weight of the TiO$_2$ of the additive is between 15% and 50% by weight of TiO$_2$; l where the dispersion of the support activated with acid and the TiO$_2$ particles are subjected to an agitation and dispersion in high shear conditions during a time of between 5 and 20 minutes;

where the dispersion at high shear is performed with mechanical shakers capable of reaching a peripheral velocity equal to or greater than 10 m/s;

where the support has an average particle size less than 44 μm; and where the TiO$_2$ particles which are dispersed in stage (iii) have an average particle size less than 100 nm.

In another embodiment, the invention relates to the composition described above, where the composition is cement, preferably where the composition is cement comprising between 0.1% and 15% by weight of the additive, and preferably between 1.0% and 6% by weight of the additive.

In another embodiment, the invention relates to the composition described above, where the composition is mortar or concrete, preferably where the composition is mortar or concrete comprising between 0.1% and 15% by weight of the additive over the weight of the binder, and preferably between 1.0% and 6% by weight of the additive over the weight of the binder.

In another embodiment, the invention relates to the composition described above, where the composition is lime mortar or mixed mortar, preferably where the composition is lime mortar or mixed mortar comprising between 0.1% and 15% by weight of the additive over the weight of the binder, and preferably between 1.0% and 6% by weight of the additive over the weight of the binder.

In another embodiment, the invention relates to the composition described above, where the composition is plaster, preferably where the composition is plaster comprising between 0.1% and 15% by weight of the additive over the weight of the binder, and preferably between 1.0% and 6% by weight of the additive over the weight of the binder.

In another embodiment, the invention relates to the composition described above, where the composition is paint, any type of coating, emulsion or protective layer, preferably paint, any type of coating, emulsion or protective layer, for its use outdoors.

In another embodiment, the invention relates to the composition described above, where the composition is paint comprising between 0.1% and a 10% by weight of the additive, and preferably between 0.5% and 4% by weight of the additive.

In another embodiment, the invention relates to the composition described above, where the composition is paint for its use outdoors comprising between 0.1% and a 10% by weight of the additive, and preferably between 0.5% and 4% by weight of the additive.

In another embodiment, the invention relates to the composition described above, where the composition is sol-gel coating, preferably where the composition is sol-gel coating comprising between 0.1% and 15% by weight of the additive, and preferably between 1.0% and 6% by weight of the additive.

DETAILED DESCRIPTION OF THE INVENTION

The objective of the invention is centred on resolving the problems found in the state of the art associated to the agglomeration of $TiO_2$ particles, mainly on a nanometric scale, as a consequence of their high surface activity by a process which is simple and easily scalable on an industrial level which makes it possible to enhance its photocatalytic activity.

The present invention relates to a process of obtainment of a photocatalytic additive mainly constituted by $TiO_2$ particles homogeneously dispersed in a pseudo-layered phyllosilicate-type clay (sepiolite and/or attapulgite). Likewise, the invention relates to the use of the photocatalytic additive containing the $TiO_2$ particles obtained by this process as photocatalytic additives in materials to give them self-cleaning, pollution reduction and disinfection characteristics, which are active even in the absence of environmental humidity.

The obtainment of homogeneously dispersed $TiO_2$ particles object of the present invention is based on the use of a clay as support, selected from the group of pseudo-layered phyllosilicates. In accordance with the invention, the clay used as support is sepiolite or attapulgite (also called palygorskite). For the object of this invention it is preferable to use the ground clay with a particle size as fine as possible to increase the accessible surface for the support of the $TiO_2$ particles. Normally, the clay is ground until a particle size less than 150 micrometers, and preferably less than 44 micrometers. An especially advantageous embodiment of this invention is when the clay particle size is less than 5 micrometers. Sepiolite and attapulgite products obtained by dry or wet grinding processes typically used for the grinding and reduction of clay particle sizes can be used, such as, for example, impact or ball mills. Products of these clays obtained by special wet micronization processes can also be used, which produce the separation of the elementary particles of the clay, without breaking its structure, and which makes it possible to expose its external surface to the maximum. Examples of these products are rheological grade sepiolite and attapulgite products obtained in accordance with the processes disclosed in patents EP0170299, EP0454222 and EP0170299).

Sepiolite is chemically a hydrated magnesium silicate with acicular morphology and ideal formula: $[Si_{12}O_{30}Mg_8(OH)_4(OH_2)_4](H_2O)_8$. The sepiolite structure is similar to that of attapulgite or palygorskite. Attapulgite is differentiated from sepiolite in that its unit cell is slightly smaller and in that part of the magnesium cations have been substituted fundamentally by aluminium cations, with smaller contents of other cations such as iron. The ideal formula of attapulgite is: $[Si_8O_{20}(Al_2Mg_2)(OH)_2(OH_2)_4](H_2O)_4$. The isomorphous substitution of the $Al^{3+}$ and $Mg^{2+}$ cations or even the $Si^{4+}$ cations of the silicate's structure by other cations may give rise to a small negative charge in the structure of the sepiolite and attapulgite silicate, which is compensated for by adsorbing cations. As a consequence of these isomorphous substitutions, these clays have an intermediate cation exchange capacity (CEC) between kaolin and the smectites, and, furthermore, their chemical composition is separated from the composition of the formula ideal. The CEC of sepiolite and attapulgite varies depending on its composition between 3 and 45 milliequivalents/100 g. The substitution of the octahedral cations in the silicate structure gives rise to the different varieties of sepiolite and attapulgite. In the case of attapulgite, the cations that may appear substituting the aluminium and magnesium are manganese, manganese and iron, manganese and zinc or sodium and iron whilst in the case of sepiolite occasionally varieties of ferric or xylitol, sodium or loughlinite, ferric nickel or falcondoite, aluminic and magnesium sepiolite have been found in nature.

The structure of these pseudo-layered phyllosilicates, with acicular or microfibrous morphology, is formed by two parallel chains of silica bound by oxygen atoms to a central layer of aluminium and/or magnesium octahedrons. These chains comprised of silica tetrahedrons are inverted every six units in the case of sepiolite and every four in the case of attapulgite giving rise to discontinuities in the octahedral layers that cause channels, called zeolitic, oriented in the direction of the c-axis of the acicular particles, with dimensions of 3.7×10.6 Å for the sepiolite and 3.7×6.4 Å for the attapulgite. As a consequence of this structure, the sepiolite and attapulgite adsorb water (zeolitic water) and other compounds (depending on the size and polarity of the molecule) not only on their outer surface but also inside the zeolitic channels.

These clays have a high specific surface due to their elongated habit, high porosity and large particle size. The total specific surface (external and internal) of these clays, calculated by theoretical models, is approximately 900 m²/g: 400 m²/g of external area and 500 m²/g of internal area in the sepiolite and 300 m²/g of external area and 600 m²/g of internal area in the attapulgite. However, the surface area of these clays accessible to the different compounds or adsorbates depends on their size and polarity, which determines the penetration capacity of the molecules in the clay's pores and channels. For example, the accessible BET surface to $N_2$ is more than 300 m²/g in the case of sepiolite and around 150 m²/g in the attapulgite.

These clays have a high density of silanol groups (—SiOH) in their external surface which are originated in the edges of the layers of silica tetrahedrons. These silanol groups are disposed lining the outer surface of these clays and give it a high degree of hydrophilicity due to their capacity to adsorb water molecules. These silanol groups can act as active adsorption centres, and may form hydrogen bridges with different molecules.

The obtainment of supported and dispersed $TiO_2$ particles may be performed using sepiolite or attapulgite minerals, or the combination of both minerals, as support. In nature, sepiolite and attapulgite minerals may appear associated with greater or lesser contents of other clays or minerals. For the obtainment of products with a suitable activity it is preferable to use a starting mineral which has a sepiolite and/or attapulgite concentration greater than 50%, and better a concentration greater than 85%, since the presence of other clays or minerals, such as calcite, dolomite, feldspar, mica, quartz or smectite, may influence the dispersion of $TiO_2$ and, therefore, the properties of the end product. Furthermore, to achieve a homogeneous dispersion of $TiO_2$ in the fibres of these pseudo-layered phyllosilicates it is recommendable to use a sepiolite and attapulgite product as support obtained by a previous grinding and wet micronizing process as disclosed in patent EP0170299, with the objective of purifying and deagglomerating the clusters of acicular particles present in these clays in nature and obtaining individualized microfibrous particles and maintaining their appearance ratio. The product obtained by the previous process allows a greater access of the $TiO_2$ particles to the outer surface of the clay.

The process of the present invention comprises a first stage of dispersion of the clay in aqueous medium. To achieve a suitable dispersion of the sepiolite and/or attapulgite particles, it is preferable to use high-shear mixing systems to achieve the best possible defibrillation of the clusters of sepiolite and/or attapulgite. Example of high-shear mixing systems are the mechanical shakers capable of reaching a peripheral velocity of at least 10 m/s.

After the clay dispersion stage, an activation stage of the clay takes place in acid medium to increase the number of Lewis and Brönsted surface acid centres of the clay, in particular silanol groups (SiOH), produced by the leaching of the magnesium and aluminium cations localized in the edges of the clay structure. The $TiO_2$ particles are anchored on those active centres to obtain a homogeneous support on the phyllosilicate surface. This activation is performed by the controlled addition of an acid until the final pH of the clay dispersion is less than 5 and preferably between 1 and 3. The acidification of the clay suspension causes the leaching of the octahedral cations (aluminium and/or magnesium) from the clay silicate structure. The optimum percentage of clay activation occurs when between 5% and 25% of the magnesium cations leach from the sepiolite structure and between 5% and 33% of the magnesium/aluminium cations from the attapulgite structure. These maximum activation percentages correspond to the complete leaching of the cations situated in the external edges of the octahedral layer of the clay. The leaching of greater percentages of octahedral cations produces structural changes that may completely amorphize the structure for high degrees of leaching. These structural changes as a consequence of excessive acid leaching also produce changes in other properties of the clay such as the loss of rheological properties. The time and the temperature of the acid activation stage of the cation depend on the leaching percentage that one wants to achieve. A typical activation treatment is achieved by the addition of an acid until a final pH of clay dispersion between 1 and 3, at a temperature between 10° C. and 35° C. during a time of 0.5 to 2 hours. The acid may be any organic or inorganic acid capable of reaching the required dispersion pH such as, for example, hydrochloric acid, sulphuric acid, nitric acid or phosphoric acid.

After the acid activation stage of the clay, the controlled addition is performed of the titanium oxide particles. The titanium oxide particles may be added in solid or, preferably in the form of a previously prepared suspension in water. The clay and $TiO_2$ dispersion is suitably stirred to obtain complete homogeneity in the clay and titanium oxide mixture. To achieve this homogeneity and dispersion, it is appropriate to use high-shear mixing systems, such as, for example, mechanical shaking capable of reaching a peripheral velocity of at least 10 m/s. Particularly suitable are rotor/stator-type dispersion systems such as colloidal mills or micro ball mills, to achieve a suitable dispersion of the aggregates of clay and $TiO_2$ particles. In this stage of the process, in addition to the dispersion, the $TiO_2$ nanoparticles are anchored on the acid centres generated on the clay surface by the acid treatment.

Depending on the application that the photocatalytic additive is intended for, the aqueous dispersion of the clay and the titanium oxide can be subjected to a filtration and drying process in a later stage to obtain the powdered product.

The titanium oxide can be directly added in the process for its high shear dispersion or it may be synthesized in a previous stage of the process by thermal treatment of a metal precursor in the form of a salt or hydroxide. The titanium oxide must be at least of micrometric size, preferably submicrometric or nanometric, in one of its three brookite, anatase or rutile phases. Preferably the $TiO_2$ phase is anatase, or a combination of anatase with the other phases, preferably rutile.

In the processes described to date in the state of the art for the support of $TiO_2$ on sepiolite, a thermal treatment is normally required, necessary to generate the phocatalytically active $TiO_2$ phase, form an inorganic foam by lyophilization or to produce the folding of the clay structure, which gives rise to modification of the properties and characteristics of the clay used as support.

The process which is used in the present invention is based on supporting a previously synthesized $TiO_2$ on the pseudo-layered phyllosilicate. Therefore, the clay maintains its rheological properties and its adsorption capacity since it is not necessary to thermally treat the supported product to generate the photocatalytically active $TiO_2$ phase. The absence of thermal treatment of the clay is especially important as it enables the additive to have photocatalytic activity even in the absence of environmental humidity, given that both the sepiolite and the attapulgite have water absorbed on the surface that may intervene in the photocatalytic decomposition reaction.

To achieve a complete dispersion of the $TiO_2$ nanoparticles and a homogeneous dispersion thereof on the sepiolite or attapulgite fibres, the mixture of the clay and the titanium oxide is performed, preferably, from the clay dispersion activated with a concentration of 2 to 30% of the clay in water and a dispersion in water of the $TiO_2$ with a concentration of 2 to 30% of the $TiO_2$ in water. Likewise, the $TiO_2$ concentration in the support (sepiolite or attapulgite) can vary from 5 to 75% by weight depending on the density of $TiO_2$ particles one wants to obtain on the surface of the clay fibres, and preferably from 10 to 50% by weight. The process of the present invention allows $TiO_2$ concentrations of up to 75% by weight to be supported on the clay without observing agglomeration. However, from the standpoint of the cost/efficacy ratio of the end product, bearing in mind the photocatalytic activity, it is preferable that the $TiO_2$ concentration is in the range of 10 to 50% by weight.

If one wants to obtain the end product in the form of dry powder, the titanium oxide dispersion supported on the clay is filtered, or separated by typical solid/liquid separation techniques, before drying to obtain the end product with the titanium oxide particles homogeneously distributed on the clay surface. The solid/liquid separation can also be performed, among other processes known in the state of the art, by centrifugation or decantation, as well as by direct evaporation via drying of the dispersion water at atmospheric pressure or at low pressure or in a vacuum. Lyophilization processes can also be used by freezing and sublimation of the water in low-pressure conditions.

Through the aforementioned process, it is possible to obtain a composite material formed by titanium oxide particles homogenously monodispersed and anchored on the clay surface used as support, where the size of the $TiO_2$ particles can reach up to 5 nm, depending on the size of the titanium oxide used in the process. It has been observed that the material obtained enhances the efficacy of the $TiO_2$ deposited on these clays with very high specific surface, and is, therefore, an advantageous material for applications where $TiO_2$ is used, such as, for example, photocatalytic applications or as opacifier.

In short, the process of the present invention is based on the support and anchoring of titanium oxide particles on active centres created by acid treatment on the surface of pseudo-layered phyllosilicates, in particular, sepiolite and attapulgite. Due to the peculiar structure of these clays, and to the process for generating Lewis and Brönsted surface acid centres, homogeneous dispersions of titanium oxide particles are obtained in controlled form with a size of up to 5 nm anchored and supported on monodispersed and homogenous form on the clay surface, with a weight content between 5% and 75% of $TiO_2$, and preferably between 10% and 50%. This process makes it possible to resolve the agglomeration problems that arise in the $TiO_2$ particles and which are greatly aggravated when the $TiO_2$ particles are of nanometric scale.

As regards the photocatalytic properties, the homogeneous dispersion of the $TiO_2$ particles in the support enables a greater contact between them and the pollutant, also absorbed on the clay surface, which enhances the photocatalytic effect as it has a greater contact area. Furthermore, due to the structure of these clays, the additive may degrade the organic material in the absence of environmental humidity using the water present or physisorbed in the clay structure as a source of OH radicals. The homogeneous dispersion of titanium oxide particles anchored and supported on sepiolite or attapulgite further enables using these composite clay-$TiO_2$ products to homogeneously introduce these photocatalytically active particles in other systems such as mortars or paints obtaining greater activity than with non-supported titanium oxide.

As previously described, the pseudo-layered phyllosilicates (sepiolite and attapulgite) used as support of the $TiO_2$ nanoparticles provide a series of advantages to the conventional photocatalytic products. The photocatalytic activity of the additive of the present invention is significantly greater than that of the $TiO_2$ products currently on the market due to the synergic effect between the $TiO_2$ nanoparticles and these clays. This greater photocatalytic activity enables that the percentages of the product obtained by the present invention that it is necessary to add to the different products are less than those of the conventional $TiO_2$ products with equal activity.

In short, the increase in the photocatalytic activity of the $TiO_2$ additive anchored and supported on sepiolite and attapulgite with respect to only using $TiO_2$ particles is fundamentally due to five phenomena:

i) Homogeneous dispersion of the $TiO_2$ nanoparticles on the surface of the sepiolite and attapulgite previously treated with acid to increase the Lewis and Brönsted acid centres, whereon the $TiO_2$ particles are anchored. Photocatalysis is a surface process: the greater the specific surface, the greater the activity of the catalyst. The fact that the $TiO_2$ nanoparticles are fixed and dispersed on the treated sepiolite and attapulgite surface, avoids these nanoparticles from being able to agglomerate forming large groups of hundreds or thousands of nanoparticles. These groups of nanoparticles have a smaller area exposed than that of the individualized nanoparticles, thus losing effective catalytic activity.

ii) The sepiolite and attapulgite, due to their physicochemical characteristics and high porosity and specific surface, are clays with high adsorption and absorption capacity. This property is fundamental in the photocatalytic decomposition processes since it allows the catalyst support (sepiolite and attapulgite) to attract and retain the compounds, for example pollutants, which will later degrade the photocatalyst. In this way, it places the catalyst in close contact with the compounds that are going to be degraded, significantly improving the diffusion process of the pollutant to the catalyst, key stage in catalysis.

iii) Another important factor that is advantageous is that these clays, sepiolite and attapulgite, are very hydrophilic and usually have a water content adsorbed on the surface of approximately 10% in normal conditions. This adsorbed water provides the OH and $H^+$ species necessary for the photocatalytic process to take place. Therefore, water from environmental humidity is not necessary for the photocatalytic reaction to take place.

iv) Another important factor that is advantageous on using $TiO_2$ anchored and supported on sepiolite and attapulgite is that the degree of hydrophilicity of these clays can be adjusted. Environmental humidity is a highly critical factor in photocatalytic decomposition processes. On the one hand, humidity is usually necessary, since it provides the $H_2O$, source of the OH and H+ necessary for the photocatalytic process to take place. But, on the other hand, the $H_2O$ molecules compete for the active sites of the catalysts with the molecules of the compounds one wants to degrade. Therefore, there is an optimum humidity for the correct functioning of the photocatalytic processes. With the use of these clays as $TiO_2$ support, it is possible to adjust the quantity of $H_2O$ that reaches the catalyst adjusting the water content present in the sepiolite and attapulgite. In the absence of environmental humidity, the water adsorbed on the hydrophilic surface of the sepiolite and attapulgite provides the necessary water molecules for the photocatalytic process. In contrast, in highly humid environments it is possible to modify the clay surface to make it less hydrophilic and avoid the excessive adsorption of water molecules that may saturate the active centres.

v) In addition to the above factors related to the photocatalytic activity of the product obtained by the process of the present invention, it is necessary to emphasize that this product maintains intact the properties of the clay used as support, for example its rheological properties. In consequence, these clays may provide the improvements in rheological properties which can be achieved with these clays, in particular sepiolite, when they are used as rheological additives to control the viscosity, or provide thixotropy or pseudoplasticity in different applications, as is the case of mortars on site (guniting, etc).

Therefore, in addition to the improvement of the photocatalytic properties of self-cleaning, deodorization, biocide and atmospheric pollution reduction, the sepiolite and attapulgite used as support of the TiO$_2$ nanoparticles also give good rheological behaviour to paints, mortars, concretes, etc. They give a thixotropic behaviour to the matrices wherein they are incorporated, allowing a decrease in the bleeding and segregation of the mixture. In this way it generates a more homogeneous and cohesive mixture which improves adherence to the substrate, the workability and the surface finish.

The product obtained by the process of the present invention can be used as additive with photocatalytic properties to provide self-cleaning, deodorization, biocide, waste water pollution reduction and atmospheric pollution reduction characteristics to different compositions and materials, such as, for example, coatings, paints, construction materials, etc. These materials and compositions may be matrices of different nature such as, for example, a resin or a polymer, either thermoplastic or thermostable, a bituminous binder, a hydraulic binder, such as cement or hydraulic lime, or a glass-ceramic or ceramic matrix. The product can also be directly used for the treatment and purification of liquid and gaseous effluents such as, for example process or waste waters. The direct use of the product may be in the form of a powdered product, for dispersing it inside the fluid, or pelletized or compacted to obtain a filler which can be used in percolation columns wherethrough the fluid to be treated is passed. If it is used in the form of powder to treat effluents, the micrometric size of the clay particles with supported TiO$_2$ makes it possible to recover the additively easier than if free and non-supported TiO$_2$ nanoparticles are used.

Furthermore, it is possible to add other components and additives to the photocatalytic additive obtained by the process of the present invention, a TiO$_2$ compound supported on sepiolite and attapulgite. For example, whitening enhancers for construction material applications with self-cleaning properties. Mortar whitening enhancing products are especially used in areas with high rainfall, where the mortars exposed to the environment may lose their white tone due to humidity. Both powdered calcium carbonate and micrometric TiO$_2$ in anatase phase have been successfully used. These additives barely increase the cost of the mixture and enhance the whiteness. Furthermore, the micrometric TiO$_2$ in anatase phase also has photocatalytic properties (although to a much less extent than the nanoparticles), so that the self-cleaning effect is slightly enhanced. The addition of superplasticizers may also be required for some applications to adjust the workability of the mixtures.

Within the construction sector, the main functionalities sought with the additive object of the present invention are self-cleaning, reducing environmental pollution and deodorization and biocide activity.

Self-cleaning is especially desired in construction components of light colours wherein the end aesthetic effect is of vital importance. This is the case of flagship buildings of cities such as town councils, auditoriums, churches, sports centres, cultural centres, etc. In these cases, the incorporation of the additive shall especially be performed in prefabricated façade panels of concrete, paints or sol-gel coatings.

Pollution reduction construction materials are of vital importance in large polluted population centres where decreasing pollution levels are a priority. There are numerous construction components wherein the additive object of the present patent can be incorporated for this purpose. It may be incorporated, for example, in concrete prefabricates such as façade panels, paving stones or street furniture, in a bed of cement applied on a bituminous road surface with open porosity, in concrete floors, etc.

Furthermore, the photocatalytic additive of the present invention has a biocide effect and may be used in facilities where this type of materials with this effect is of interest and entails an added value, such as hospitals and health centres, hypermarkets, shopping centres, swimming pools and sports centres, food, agriculture and cattle farming industries, etc. This additive can be added to all components of these facilities provided that they are exposed to ultraviolet radiation to ensure the photocatalytic effect. For example, in concrete floors, single-layer mortars, façade panels, etc.

In all the aforementioned applications that are in cement, lime or plaster base, the photocatalytic additive will be added so that there is between 0.05 and 5% of TiO$_2$ nanoparticles by weight with respect to the binder (cement, lime or plaster). Preferably, it will be added in a percentage of between 0.5 and 2% TiO$_2$ nanoparticles by weight with respect to the binder. It must be reminded that the titanium oxide concentration in the support (sepiolite or attapulgite) is adjusted to a concentration of between 5 to 75% by weight, and preferably 10 to 50% by weight. Therefore, if it is, for example, an additive prepared with 50% TiO$_2$ on sepiolite, there will preferably be between 1 and 4% of this additive added to the mixture (by weight with respect to the binder).

In the applications in sol-gel coatings, the additive is added in percentages between 0.1 and 15% by weight with respect to the total composition. Preferably in a percentage of between 1 and 6%. And in the case of the paints in percentages of between 0.1 and 10% with respect to the total mass, preferably between 0.5 and 4%.

The additive object of the present invention will be added either in powder or dispersed previously in a solvent (water, alcohol, etc.) in any proportion depending on the processing and of the application desired with the additive object of the present invention.

Throughout the description and the claims the word "comprises" and its variants are not intended to exclude other technical characteristics, additives, components or steps. For persons skilled in the art, other objects, advantages and characteristics of the invention will be inferred in part from the description and in part from the practice of the invention. The following figures and examples are provided by way of illustration, and are not intended to limit the present invention.

EXAMPLES

Example 1: Dispersion of TiO$_2$ Nanoparticles on Sepiolite

Figure 1:
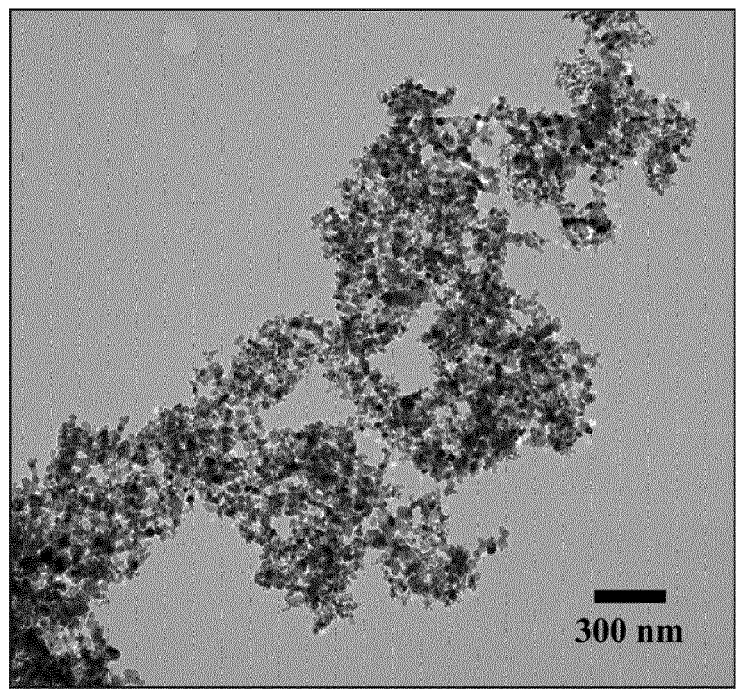
FIG. 1. Shows a transmission electron micrograph image of the titanium oxide particles of nanometric size agglomerated due to the high surface energy they have.

In this example commercial titanium oxide nanoparticles of anatase phase have been used, with an average size of 21 nm. FIG. 1 shows a transmission electron micrograph of the commercial TiO$_2$ nanoparticles used which shows the presence of large agglomerates.

Firstly, a dispersion is prepared of micronized sepiolite with a particle size with 99.9% less than 44 μm and 95% less than 5 μm, in water with a solid concentration of 6% (60 g of dry base sepiolite for 1000 g of pregel), mixed by a Cowles-type high shear mixer for 10 minutes, using a peripheral velocity of 18 m/s. The dispersion of clay in water has an initial pH of 8.9, and it is acidified to a pH of 3, by the addition of 50% sulphuric acid. After the addition of the acid the dispersion is stirred for another 10 minutes. On the other hand, a dispersion is prepared of the commercial titanium oxide nanoparticles in water at a weight concentration of 6% stirring with a Cowles mixture with a peripheral velocity of 18 m/s for 10 minutes. The TiO$_2$ dispersion is added to the acidified sepiolite pregel to obtain a final concentration of TiO$_2$ in sepiolite of 35% by weight, and it is mixed by a high shear mixer at a peripheral velocity of 18 m/s for 10 minutes to guarantee an anchoring and homogeneous dispersion of the titanium oxide on the sepiolite fibres. The dispersion is filtered and the sepiolite with TiO$_2$ is dried at 100° C. until a final humidity of 10%.

Figure 2:
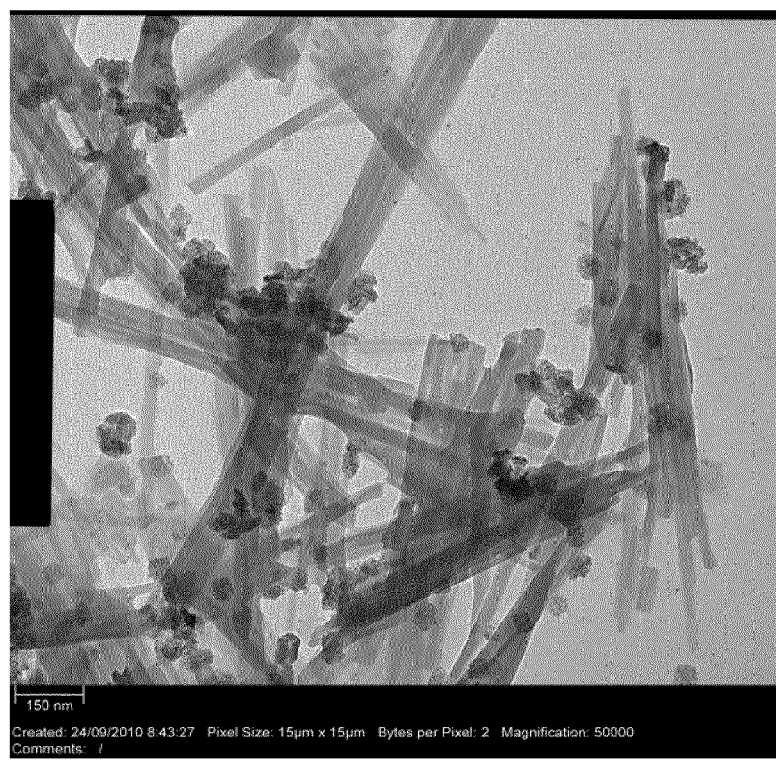
FIG. 2. Shows a transmission electron micrograph image of titanium oxide particles anchored and supported homogeneously in sepiolite following the process described in the invention, with a TiO$_2$/sepiolite weight ratio of 35/65.

As a result monodispersed nanoparticles are obtained supported throughout the sepiolite fibres as is observed in the attached transmission electron micrograph (FIG. 2).

Example 2: Photocatalytic Effect of the TiO$_2$ Product Supported on Sepiolite A dispersion is prepared of a rheological grade sepiolite obtained by the process disclosed in patent EP0170299, trade name PANGEL, 6% in water by a mechanical blade shaker which rotates at 1,000 rpm for 10 minutes, and is then acidified at pH 3 by the addition of 50% sulphuric acid. This dispersion is followed by stirring for another 10 minutes to achieve the surface activation of the sepiolite surface. An aqueous dispersion with 6% commercial TiO$_2$ nanoparticles previously prepared as indicated in example 1 is added to the previous dispersion, so that the final TiO$_2$/sepiolite ratio is 50/50. The resulting suspension is vigorously mixed in a Grindomix-type ball mill with zircon balls of between 1.6 and 2.4 mm in diameter for 10 minutes to achieve sufficient shear to completely defibrillate the sepiolite clusters and totally disperse the TiO$_2$ nanoparticles anchored to the acid centres of the exposed surface of the sepiolite. Next, the product was filtered and dried at 105° C., until a final humidity of 10%.

Figure 3:
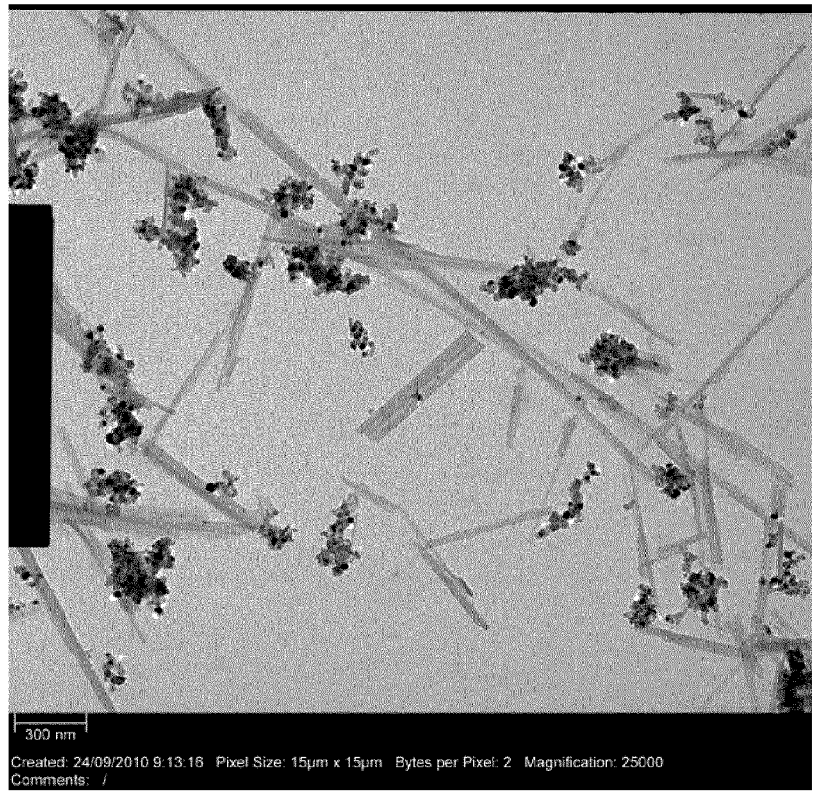
FIG. 3. Shows a transmission electron micrograph image of sepiolite fibres with titanium oxide nanoparticles of approximately 21 nm of size supported and homogeneously distributed with a TiO$_2$/sepiolite weight ratio of 50/50.

As is observed in the transmission electron micrograph (FIG. 3), the process of acid activation of the sepiolite together with the high shear mixing makes it possible to obtain nanoparticles homogeneously distributed throughout the sepiolite fibres even at a titanium oxide concentration of 50% by weight with respect to the sepiolite.

To determine the effect of the homogeneous dispersion of the TiO$_2$ particles supported on sepiolite on its photocatalytic activity, two slabs were compacted in the same conditions, to have the same surface roughness, thickness and TiO$_2$ concentration, a commercial titanium oxide in anatase phase and another of this same oxide supported on sepiolite, obtained as indicated in this example, using in both cases KBr to compact the powder. The slabs obtained are homogeneously impregnated with a Rhodamine B solution used as colouring agent and subjected to different times (0, 30 min., 1, 3 and 6 hours) of exposure to UV radiation with a UVA-340 light lamp. A faster degradation of the colouring agent was observed as a result of the increase in the contact surface of the TiO$_2$ nanoparticles as they are monodispersed in the sepiolite.

Example 3: Dispersion of the Sepiolite Product with TiO$_2$ in a Mortar Matrix The present example compares the dispersion in a mortar of the sepiolite product with 50% TiO$_2$ nanoparticles (sepiolite/TiO$_2$ 50/50), obtained according to example 2, in comparison with the dispersion of non-supported TiO$_2$ nanoparticles.

The process of addition of the photocatalytic additive to the mortar, both of commercial non-supported TiO$_2$ nanoparticles and the sepiolite/TiO$_2$ additive 50/50, has consisted of firstly dispersing the photocatalytic additive in water by mechanical shaking. To do this, a foot shaker has been used with a shaft rotating at 4,000 rpm for 15 minutes and with the rotor-stator module. Once the photocatalytic additive has been dispersed in water, the mixture with the cement and the sand are mixed in a conventional mortar mixer.

Figure 4:
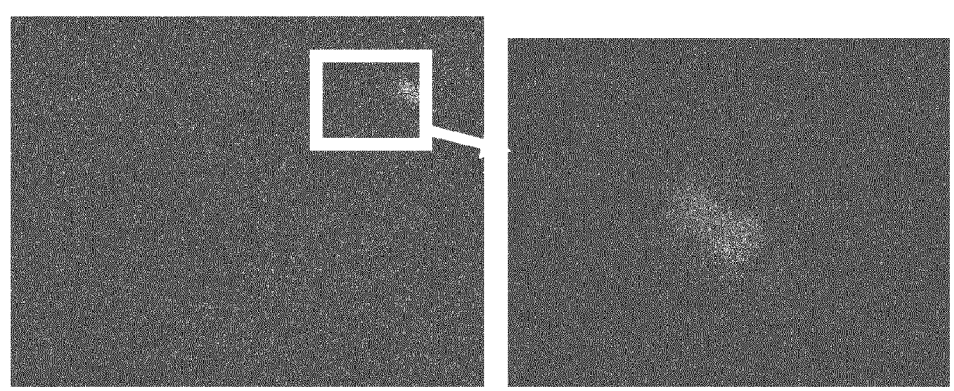
FIG. 4. Shows an electron scanning microscope image of a mortar whereto non-supported TiO$_2$ nanoparticles have been added, with the distribution of the titanium performed with the EDX probe (mapping). The dispersion of TiO$_2$ nanoparticles can be observed in mortar with the presence of large and compact agglomerates. Left: 1500 magnifications. Right: 6000 magnifications.
Figure 5:
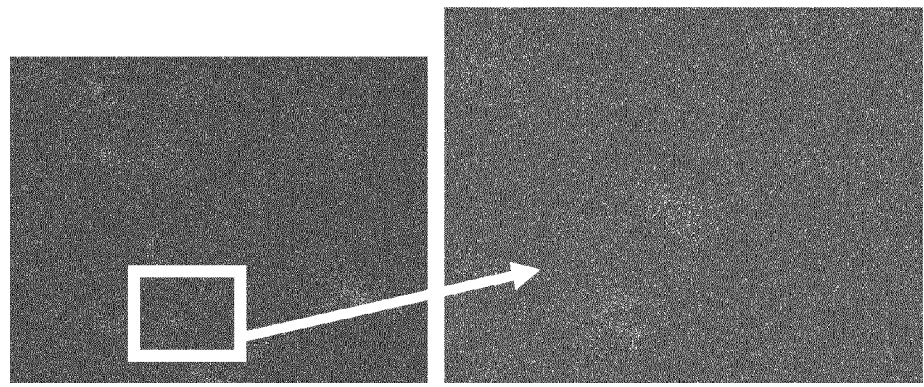
FIG. 5. Shows an electron scanning microscope image of a mortar whereto a product has been added following the process described in the invention with 50% by weight of TiO$_2$ nanoparticles anchored and supported on sepiolite. It shows the distribution of the titanium performed with the EDX probe (mapping). It is possible to observe the correct dispersion of TiO$_2$ nanoparticles/Sepiolite 50/50 in mortar with few and not very compact agglomerates.

The analysis of the dispersion of the different photocatalytic additives in mortar has been performed by a study of the distribution, or mapping, of titanium by the EDX of the electron scanning microscopy. FIGS. 4 and 5 show the result of said analysis. It can be seen how in the case of the commercial non-supported TiO$_2$ nanoparticles large compact agglomerates of nanoparticles are formed. In contrast, in the case of the sepiolite/TiO$_2$ product 50/50 the dispersion is more homogeneous and, although there are some agglomerates, they are much less compact.

The better dispersion is translated into a greater photocatalytic efficacy, as can be verified in the following examples.

Example 4: Simulation of a Real Mortar Façade with White Cement. Influence of the Photocatalytic Additive in the Self-Cleaning Properties of the Mortars. Qualitative Study A qualitative method has been developed consisting of simulating a real façade and visually evaluating its self-cleaning effect in normal atmospheric conditions. This method has been based on standard ASTM G7-97.

Figure 6:
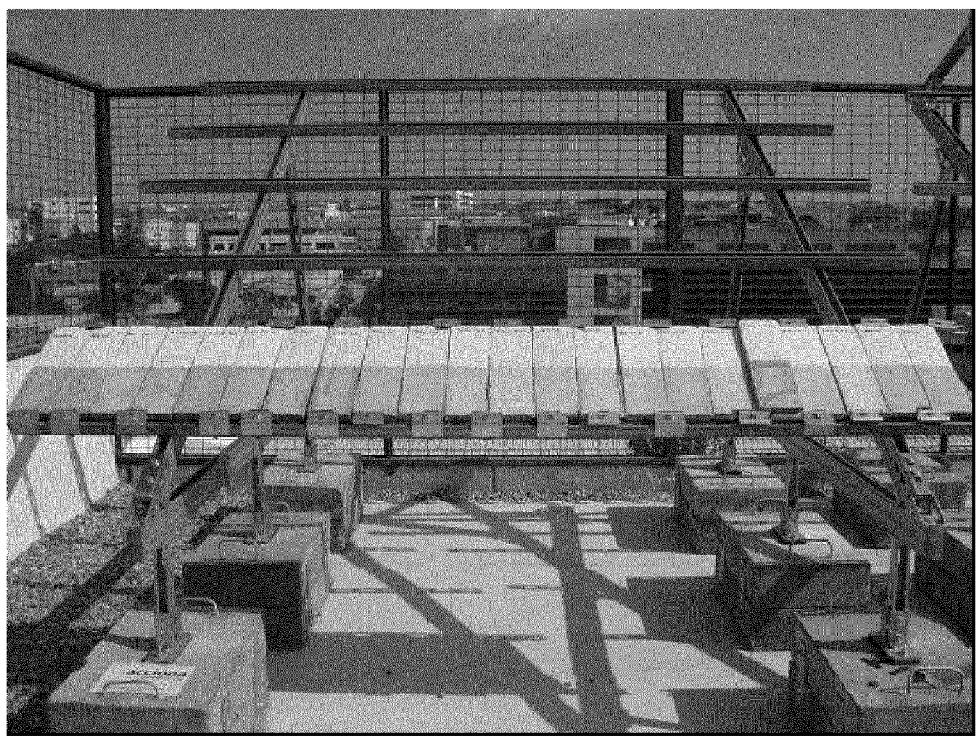
FIG. 6. Shows an experimental device to assess the self-cleaning of the materials developed; the method consists of a simulation of a real façade of mortar with white cement.

The method consists of the following: mortar specimens are prepared with the dosages considered appropriate (with and without photocatalytic additives). Once the specimens are prepared, a part of their surface is impregnated with an organic pollutant (rhodamine), simulating dirt, and the other part is left intact. The objective is to study how the organic pollutant degrades and visually analyse how the part that is not impregnated dirties over time due to environmental dirt. The specimens thus prepared are placed on the roof with an angle of 45° with respect to the horizontal. The self-cleaning is visually analysed in determined periods of time (FIG. 6).

The specimens analysed have dimensions of 10×40×2 cm. Specimens have been prepared with BL A-L 42.5 white cement and different sepiolite products with $TiO_2$ nanoparticles prepared as described in example 2, and added at different percentages. Furthermore, other types of additives have been added: 1) superplasticizers to improve the workability of the fresh mortar and 2) whiteners to enhance the whiteness of the specimens. Micrometric titanium has been chosen as whitener; however, despite being $TiO_2$, its photocatalytic effect is minimal due to its size. By way of comparison, a sepiolite has been used with $TiO_2$ nanoparticles synthesized in the clay fibres in accordance with the process described in patent WO2005035124. The dosages prepared are listed in the following table.

| Id* | Type of Photocatalytic additive | Dosage of photocatalytic additive (%) | Dosage of whitener Micrometric $TiO_2$ (%) | Total content of $TiO_2$ and type (%) |
|---|---|---|---|---|
| A | — | — | — | |
| B | — | — | 1 | 1, micrometric |
| C | 33% SepTiO$_2$ (a) | 1.5 | — | 0.5, nanometric |
| D | 50% SepTiO$_2$ (b) | 1 | — | 0.5, nanometric |
| E | 33% SepTiO$_2$ (a) | 3 | — | 1, nanometric |
| F | 50% SepTiO$_2$ (b) | 2 | — | 1, nanometric |
| G | 33% SepTiO$_2$ (a) | 3 | 1 | 1, nanometric + 1, micrometric |
| H | 50% SepTiO$_2$ (b) | 2 | 1 | 1, nanometric + 1, micrometric |
| I | 33% SepTiO$_2$ Synthesis (c) | 3 | 1 | 1, nanometric + 1, micrometric |
| J | nanoTiO$_2$ commercial (d) | 1 | 1 | 1, nanometric + 1, micrometric |

*All the samples use BL A-L 42.5R cement, standardized sand according to standard UNE EN 196-1 (3:1 ratio with the cement) and a water/cement ratio of 0.5.
(a): 33% SepTiO$_2$: Sepiolite/TiO$_2$ product with 33% TiO$_2$ prepared according to example 2
(b): 50% SepTiO$_2$: Sepiolite/TiO$_2$ product with 50% of TiO$_2$ prepared according to example 2
(c): 33% SepTiO$_2$ synthesis: Sepiolite product with 33% TiO$_2$ nanoparticles prepared by direct synthesis of the TiO$_2$ on the sepiolite as described in patent WO2005035124
(d): Commercial TiO$_2$ nanoparticles not supported on sepiolite As the method is qualitative and can only be appreciated correctly in situ or by colour photographs, it is necessary to establish a qualitative scale. Said scale is as follows:
1—Intense pink colouring.
2—Moderate pink tonality.
3—Slight pink tonality.
4—Traces of pink colouring can be observed.
5—No colouring is observed.

The following table shows the results of bleaching/self-cleaning obtained in accordance with the established scale.

| Id | t = 0 | t = 1 day | t = 2 days | t = 3 days | t = 5 days |
|---|---|---|---|---|---|
| A | 1 | 2 | 2 | 2 | 3 |
| B | 1 | 2 | 2 | 3 | 3 |
| C | 1 | 4 | 4 | 5 | 5 |
| D | 1 | 3 | 4 | 4 | 5 |
| E | 1 | 4 | 5 | 5 | 5 |
| F | 1 | 3 | 5 | 5 | 5 |
| G | 1 | 4 | 5 | 5 | 5 |
| H | 1 | 3 | 5 | 5 | 5 |
| I | 1 | 3 | 4 | 4 | 5 |
| J | 1 | 3 | 4 | 4 | 5 |

Analysing the results the following can be concluded:
In all cases the sepiolite-based photocatalytic additive achieves a faster self-cleaning than the samples without photocatalytic additive.
There is faster self-cleaning with greater percentages of photocatalytic additive.
The additive consisting of sepiolite with 33% $TiO_2$ gives faster self-cleaning than sepiolite with 50% $TiO_2$.
The product consisting of sepiolite with 33% $TiO_2$ nanoparticles synthesized directly on the sepiolite according to patent WO2005035124 has a self-cleaning activity appreciably greater than that obtained with the photocatalytic additive G with the same $TiO_2$ nanoparticle content but obtained according to the process described in this invention. These results confirm the action mechanism of the additive proposed in the patent, since the sample containing $TiO_2$ nanoparticles synthesized in sepiolite does not have rheological properties nor the water absorbed in the clay structure which would act enhancing the degradation reaction of the organic pollutant, since the $TiO_2$ nanoparticles are obtained after the thermal treatment of the clay at high temperature (700° C.), as disclosed in patent application WO2005035124. Furthermore, the sepiolite with $TiO_2$ synthesized on its surface appreciably yellow the mortar, despite the addition of whitener.
With the same $TiO_2$ content, product J with commercial non-supported $TiO_2$ nanoparticles gives a self-cleaning activity that is appreciably less than that obtained with products G and H with the $TiO_2$ anchored and supported on sepiolite following the process disclosed in this invention. This is due to the fact that the dispersion in the mortar is much more heterogeneous in the case of non-supported $TiO_2$ nanoparticles.
The addition of micrometric $TiO_2$ achieves a whitening effect which is observed in the samples. However, the addition of micrometric $TiO_2$ used as whitener does not cause a significant improvement in the self-cleaning effect in the case of nanometric $TiO_2$ supported on the sepiolite. Indeed, an effect of the micrometric $TiO_2$ is only observed on the self-cleaning activity in the case that the sample does not have sepiolite,
Due to the addition of the sepiolite-based photocatalytic additive to the cement, it is necessary to use a superplasticizer in the formulation that does not interfere in the photocatalytic properties.

Example 5: Accelerated Study with UV Light Influence of the Photocatalytic Additive in the Self-Cleaning Properties of the Mortars. Semi-Quantitative Study with Analytical Software The quantification of the self-cleaning activity of photocatalytic materials has been carried out by the test detailed below. Said test is based on the initial preparation of an organic colouring agent solution, specifically, methylene blue, which is applied on the surface to be studied. Next, UV light is irradiated (500 W UV light bulbs) on the samples prepared and it is studied how the surface loses the initially acquired blue surface and recovers its initial appearance. Photographs are taken at various times and, from these, the self-cleaning capacity of a surface associated to the photocatalytic phenomena that occur is calculated. The quantification is carried out by software which analyses the captured images of the materials tested at different times, calculating the percentage of bleaching after being exposed to ultraviolet light. The software quantifies as 100% bleaching if the same tone is reached of a reference mortar without staining by methylene blue and 0% as a reference specimen recently stained with methylene blue.

The samples tested by this method are the following:

| Id* | Type of Photocatalytic additive | Dosage of photocatalytic additive (%) | Real $TiO_2$ Content (%) |
|---|---|---|---|
| 1 | — | 0 | 0 |
| 2 | 50% SepTiO$_2$ (a) | 1.5 | 0.75 |

(a): 50% SepTiO$_2$: Sepiolite/TiO$_2$ product with 50% TiO$_2$ prepared according to example 2

The results obtained from the material with the sepiolite-based photocatalytic additive and a conventional mortar without additive are detailed below:
   Material 1 "conventional mortar without additive" achieves 8% bleaching in 240 minutes of irradiation; and
   Material 2 "mortar with sepiolite-based self-cleaning additive" achieves 21% bleaching in 240 minutes.

The 8% bleaching detected in the sample without additive is due to the degradation undergone by the methylene blue from UV irradiation, without this effect having anything to do with the photocatalytic activity. Therefore, the difference between both tests performed in parallel is due to the self-cleaning photocatalytic capacity of the material developed with the sepiolite-based additive, whose value is 13%, in the test conditions.

Example 6: NOx Pollution Reduction Tests. Quantitative

The method used basically consists of making an airstream with a known quantity of NOx pass through a hermetic chamber containing the mortar specimens with photocatalytic additive. It analyses the evolution of the NOx concentration with and without UV radiation to determine the photocatalytic efficacy of the specimens introduced in the chamber.

A heated analyser of nitrogen oxides was used to determine the concentration of nitrogen oxides by a reference method, CLD-700-AL-NO/NOx, mark ECO PHYSICS, which used the principle of chemiluminescence measurement. The test is performed at four different relative humidities of air to study the behaviour of the specimens since the relative humidity of the air is a factor which influences the process differently depending on the nature of the specimen. Furthermore, the specimens were washed with distilled water and the concentration of nitrates and nitrites of said leachate was analysed. The method used for this analysis is described in standard UNE-EN-ISO 10304-1 which uses ion chromatography with chemical suppression.

The following equations have been used to calculate the NOx elimination performance and the oxidation of NO to $NO_2$.

Percentage of $NOx$ elimination $$\frac{[NO_x]_{in} - [NO_x]_{out}}{[NO_x]_{in}} \times 100$$

Percentage of Oxidation of NO to $NO_2$ $$\frac{[NO_2]_{out}}{[NO]_{in}} \times 100$$

The suffixes "in" and "out" in the previous formulas refer to the concentrations in the input (in) and output (out) streams, respectively.

The mortars tested are described in the following table:

| Mortar | Cement | Sand (standardized according to standard UNE EN 196-1): cement | Water/cement ratio | Photo-catalytic additive | Real $TiO_2$ Content (%) |
|---|---|---|---|---|---|
| White | BL A-L 42.5 R | 3:1 | 0.5 | — | — |
| 50% SepTiO$_2$ (a) | BL A-L 42.5 R | 3:1 | 0.5 | 1.5% SepTiO$_2$. | 0.75 |
| TX Aria (b) | Cement TX Aria | 3:1 | 0.5 | TiO$_2$ nanoparticles | 3.2 (according to FRX analysis) |

(a) Mortar containing Sepiolite/TiO$_2$ with 50% TiO$_2$ obtained according to example 2 as photocatalytic additive.
(b) Mortar containing TX Aria commercial cement which has the addition of TiO$_2$ nanoparticles as photocatalytic additive.

The activity of the photocatalytic additive sepiolite/TiO$_2$ with 50% TiO$_2$ obtained by the process disclosed in the present invention has been compared with a commercial photocatalytic mortar, TX Aria.

The following table shows the NOx pollution reduction results obtained in the tests, at different relative humidities.

| Mortar | | Percentage of relative humidity | | | |
|---|---|---|---|---|---|
| | | 5% | 25% | 50% | 75% |
| White | NOx elimination | 3.4 | 2.7 | 0.3 | 2.1 |
| | NOx oxidation | 7.3 | 7.6 | 6.4 | 6.2 |
| 50% SepTiO$_2$ | NOx elimination | 48.3 | 42 | 36.0 | 35.6 |
| | NOx oxidation | 9.2 | 10.2 | 11.4 | 11.5 |
| TX Aria | NOx elimination | 53.5 | 43.3 | 38.4 | 35.7 |
| | NOx oxidation | 6.8 | 8.9 | 10.2 | 10.9 |

In light of the results obtained it can be verified that:
Both the mortar prepared with the sepiolite-based photocatalytic additive obtained according to the present invention and the commercial mortar (TX Aria) have a much greater NOx pollution reduction capacity than the white mortar.
The sample of Sepiolite/TiO$_2$ 50/50 added to the mortar in a percentage of 1.5% has an activity similar to the sample prepared with TX Aria cement, which contains a greater percentage of TiO$_2$.
In the white mortar, the percentage of NOx oxidized is much greater than that eliminated. In the other two samples, both in the sepiolite-based additive and in TX Aria, the quantity of NOx eliminated is much greater than that oxidized.

The photocatalytic activity of NOx elimination decreases as the humidity in which the test is performed increases.

Example 7: TiO$_2$ Product Supported on Sepiolite without Acid Activation

To determine the effect of acid activation of the pseudo-layered phyllosilicate on the photocatalytic activity of the sepiolite product with supported TO$_2$, a product was prepared similarly to that described in example 2, but wherein the acid activation stage of the sepiolite was omitted:

A dispersion was prepared of a rheological grade sepiolite obtained by the process disclosed in patent EP0170299, trade name PANGEL, 6% in water by a mechanical blade shaker which rotates at 1,200 rpm for 10 minutes. Omitting the acidification stage, an aqueous dispersion of 6% commercial TiO$_2$ nanoparticles previously prepared as indicated in example 1 was added to the previous dispersion, so that the final sepiolite/TiO$_2$ ratio was 50/50. The resulting suspension was vigorously mixed in a Grindomix-type ball mill with zircon balls between 1.6 and 2.4 mm in diameter for 10 minutes to achieve sufficient shear to completely defibrillate the sepiolite clusters and totally disperse the TiO$_2$ nanoparticles anchored to the acid centres of the exposed surface of the sepiolite. Next, the product was filtered and dried at 105° C., until a final humidity of 10%.

Another product was also prepared following the same process but with a sepiolite/TiO$_2$ ratio of 67/33, i.e. with 33% by weight of TiO$_2$. These products were used as photocatalytic additives in example 8.

Example 8: Quantitative Test of Toluene Pollution Reduction

The method used for this analysis basically consists of subjecting the mortars prepared to an airstream with a known concentration of toluene under UV radiation (5 mW/cm$^2$). Samples are taken of the air stream at different times: 0, 2.5, 5 and 21 hours, and the toluene concentration was analysed by chromatography to determine the progressive elimination of toluene. The equipment used to determine the toluene concentration is a gas chromatograph with mass detector (GC-MS).

The experimental device used to carry out the test basically consists of a chamber with a 6-liter volume with a Pyrex glass window, to introduce the UV radiation, wherein pressurized air and toluene are loaded. It has a pipe and a pump for total recirculation. The recirculation capacity is 30 L/min. To calculate the toluene elimination performance, the following equation has been used.

$$\frac{[Tol]_0 - [Tol]_t}{[Tol]_0} \times 100$$

The suffixes 0 and t of the previous equation refer to the toluene concentrations in the airstream at time 0 and time t, respectively.

The mortars tested are described in the following table:

| Mortar | Cement | Sand (standardized according to standard UNE EN 196-1): cement | water/cement ratio | Photocatalytic additive | Real TiO$_2$ content (%) |
|---|---|---|---|---|---|
| White | BL A-L 42.5 R | 3:1 | 0.5 | — | — |
| 33% SepTiO$_2$ (without activation) (a) | BL A-L 42.5 R | 3:1 | 0.5 | 2.3% of 33% SepTiO$_2$. | 0.75 |
| 33% SepTiO$_2$ (activated) (b) | BL A-L 42.5 R | 3:1 | 0.5 | 2.3% of 33% SepTiO$_2$. | 0.75 |
| 50% SepTiO$_2$ (without activation) (c) | BL A-L 42.5 R | 3:1 | 0.5 | 1.5% of 50% SepTiO$_2$. | 0.75 |
| 50% SepTiO$_2$ (activated) (d) | BL A-L 42.5 R | 3:1 | 0.5 | 1.5% of 50% SepTiO$_2$. | 0.75 |
| Commercial TiO$_2$ (e) | BL A-L 42.5 R | 3:1 | 0.5 | 0.75% TiO$_2$ of EVONIK | 0.75 |
| TX Aria (f) | TX Aria cement | 3:1 | 0.5 | TiO$_2$ nanoparticles | 3.2 (according to FRX analysis) |

(a): 33% SepTiO$_2$ (without activation): sepiolite/TiO$_2$ product with 33% TiO$_2$ prepared according to example 7 omitting the acid activation stage
(b): 33% SepTiO$_2$ (activated): sepiolite/TiO$_2$ product with 33% TiO$_2$ prepared according to example 2
(c): 50% SepTiO$_2$ (without activation): sepiolite/TiO$_2$ product with 50% TiO$_2$ prepared according to example 7 omitting the acid activation stage
(d): 50% SepTiO$_2$ (activated): sepiolite/TiO$_2$ product with 50% TiO$_2$ prepared according to example 2
(e): commercial TiO$_2$ nanoparticles supplied by Evonilk.
(f) Mortar containing TX Aria commercial cement which has the addition of TiO$_2$ nanoparticles as photocatalytic additive.

The following table shows results obtained of toluene pollution reduction after 21 hours of the test.

| Mortar | Percentage of toluene pollution reduction after 21 hours in the photocatalytic chamber (%) | Percentage of pollution reduction/real TiO$_2$ percentage ratio |
|---|---|---|
| White | 7 | 9 |
| 33% SepTiO$_2$ (without activation) (a) | 50 | 67 |
| 33% SepTiO$_2$ (activated) (b) | 73 | 97 |
| 50% SepTiO$_2$, (without activation) (c) | 67 | 89 |
| 50% SepTiO$_2$ (activated) (d) | 99 | 132 |
| Commercial TiO$_2$ (e) | 56 | 75 |
| TX Aria (f) | 69 | 22 |

In light of the results obtained it can be concluded that:
All samples containing photocatalytic additives have a toluene pollution reduction capacity much greater than mortar without additive.
The samples of mortar containing the TiO$_2$-based additive supported on sepiolite are more active than the commercial ones based on nanometric TiO$_2$ directly dispersed in the mortar matrix with the same TiO$_2$ content.

The samples of mortar with sepiolite-based additive have a toluene pollution reduction capacity similar to the mortar made with the TX Aria cement, but the activity/$TiO_2$ ratio is much higher in the case of sepiolite-based additives, which shows the greater efficacy of the $TiO_2$ supported on sepiolite.

The sepiolite product with 33% supported $TiO_2$ has slightly less activity than the sepiolite product containing 50% supported $TiO_2$ (with the same $TiO_2$ content).

The sepiolite-based products treated to generate a greater number of acid centres and silanol groups on the surface, obtained by acid activation treatment, have significantly greater activity than the sepiolite-based products not activated with acid.

Example 9: Sol-Gel Coatings

Since photocatalysis is a superficial phenomenon there is also the possibility of incorporating the $TiO_2$ nanoparticles supported on sepiolite on the surface of mortar or other materials via a coating.

The coatings used in the present example are based on sol-gel technology using silicon alkoxides as reaction precursors. These precursors, once dissolved in alcohol, are hydrolyzed in water to form their respective silanes and later undergo the condensation reaction.

Thus, coatings with different percentages of the sepiolite-based photocatalytic additive were applied to conventional mortars with white cement (Sepiolite/$TiO_2$), and their self-cleaning was evaluated after being dirtied with an organic pollutant (rhodamine). This staining simulates the dirt deposited in controlled manner on the surface of said specimens. The photocatalytic activity of self-cleaning was determined according to the process described in Example 4 of the present patent, based on Standard ASTM G7-97. Exposure to solar radiation caused the disappearance of said stain with the passage of time, the material recovering its initial appearance.

The results obtained from this test are included in the following table.

Self-cleaning results of the different samples of white mortar with sol-gel coating.

| ID | Silicon alkoxide (mL) | Alcohol (mL) | Water (mL) | Percentage of Sepiolite/$TiO_2$ 50/50 with respect to the quantity of alcohol (%) | Time until achieving surface cleaning (hours) |
|---|---|---|---|---|---|
| 1 | 13.73 | 36.87 | 12.29 | 0 | 2,000 |
| 2 | 13.73 | 36.87 | 12.29 | 10 | 480 |
| 3 | 13.73 | 36.87 | 12.29 | 20 | 168 |
| 4 | 13.73 | 36.87 | 12.29 | 30 | 24 |

In light of the results, it can be concluded that:

All the mortars coated with the sol-gel solution containing sepiolite-based photocatalytic additive with supported $TiO_2$ self-clean much before those coated with sol-gel without photocatalytic additive.

The greater the content of sepiolite with $TiO_2$ in the sol-gel solution, the sooner the degradation occurs of the organic colouring agent in the mortars coated with said sol-gel coatings.

Example 10: Rheological Modification of Concretes

As commented above, the photocatalytic additive of the present invention has the quality of being a concrete viscosity regulator, in addition to providing pollution reduction and self-cleaning properties.

The present example shows the rheological effect of the sepiolite-based photocatalytic additives with supported $TiO_2$.

Two concretes have been prepared, one with the photocatalytic additive and another without the same additive. The dosage has been designed so that the aggregates are segregated, to be able to evaluate the efficacy of the photocatalytic additive as rheological additive to avoid segregation in the concrete. The following table shows the two formulations prepared.

| Reference | Dosage per m³ Standard | Real dosage Mixed with 0% Sepiolite/$TiO_2$ | Real dosage with sepiolite Mixed with 1.5% Sepiolite/$TiO_2$ |
|---|---|---|---|
| Volume mixed | 1 m³ | 15 L | 15 L |
| Cement, kg | 300 | 4.50 | 4.50 |
| Water, kg | 222 | 3.35 | 3.35 |
| a/c | 0.74 | 0.74 | 0.74 |
| Quartzite sand, kg | 1137 | 17.1 | 17.1 |
| Quartzite gravel, kg | 886 | 13.3 | 13.3 |
| Plasticizer, % | 1 | 1 | 1 |
| Plasticizer, kg | 3.0 | 0.045 | 0.045 |
| Sepiolite/$TiO_2$ 50/50 % | — | 0.0 | 1.54 |
| Sepiolite/$TiO_2$ 50/50, kg | — | 0.0 | 0.06 |

Figure 7:
FIG. 7. Shows a mixture of concrete with a high water/cement ratio the Abrams cone whereof gives a value of 22 cm and shows a segregated appearance.
Figure 8:
FIG. 8. Shows the same mixture of concrete of the previous figure but after incorporating 1.5% of TiO$_2$/Sepiolite 50/50 in the mixture; an Abrams cone of 8 cm is observed without segregation.

FIGS. 7 and 8 show the result of the addition of the additive in the concrete's rheology. As can be clearly observed in the above figures, segregation occurs in the absence of the sepiolite-based additive and the Abrams cone obtained is 22 cm. In the case of the dosage with the additive (Sepiolite/$TiO_2$) it can be verified how the concrete's appearance is very good, there is no segregation and a cone of 8 cm is obtained, which is manageable and workable.

It can be concluded that in addition to providing photocatalytic properties, the additive object of the present invention also acts as a rheological modifier for concretes.

Furthermore, the mechanical properties of the concrete are not harmed by the addition of the sepiolite-based photocatalytic additive with supported $TiO_2$, as can be seen in the following table.

| Reference | 28-day resistance to compression (Mpa) |
|---|---|
| Mixed 0% Sepiolite/$TiO_2$ 50/50 | 26 |
| Mixed 1.5% Sepiolite/$TiO_2$ 50/50 | 25 |

This example shows the dual usefulness of the sepiolite-based additive with supported $TiO_2$ as photocatalytic additive and as rheological modifier in concretes.

The invention claimed is:

1. A process for the preparation of an additive, where the additive comprises $TiO_2$ particles supported and dispersed on a pseudo-layered phyllosilicate support, comprising the following stages:
   (i) the dispersion in water of the support with high shear;
   (ii) the acid activation of the support of stage (i); and (iii) the addition of the TiO$_2$ particles on the support of stage (ii) with high-shear mixing,
wherein high shear is performed with a high shear dispersion system capable of developing a peripheral velocity in the rotor greater than 10 m/s and which creates a shear velocity greater than 2,000 s$^{-1}$; and
wherein the process does not comprise a thermal treatment stage at temperatures above 350° C.

2. The process according to claim 1, further comprising the following stage after stage (iii):
(iv) solid/liquid separation of the support with the TiO$_2$ particles of the dispersion liquid, and later elimination of the residual water that remains in the support with the TiO$_2$ particles by drying at atmospheric pressure, at low pressure or in a vacuum.

3. The process according to claim 2, where solid/liquid separation of the support with the TiO$_2$ particles is performed by a filtration.

4. The process according to claim 1, where the support is sepiolite or attapulgite.

5. The process according to claim 4, where the support is rheological grade sepiolite or rheological grade attapulgite.

6. The process according to claim 1, where the TiO$_2$ particles within the additive are selected from anatase phase, rutile phase, brookite phase and a mixture thereof.

7. The process according to claim 4, where the support is activated by the addition of an acid which leaches between 5% and 25% of the magnesium cations from the sepiolite.

8. The process according to claim 4, where the support is activated by the addition of an acid which leaches between 5% and 33% of the magnesium/aluminium cations from the attapulgite.

9. The process according to claim 1, where the quantity of TiO$_2$ particles added in stage (iii) to the dispersion of the support activated with acid is adjusted so that the concentration by weight of the TiO$_2$ of the additive is between 5% and 75% by weight of TiO$_2$.

10. The process according to claim 9, where the quantity of TiO$_2$ particles added in stage (iii) to the dispersion of the support activated with acid is adjusted so that the concentration by weight of the TiO$_2$ of the additive is between 15% and 50% by weight of TiO$_2$.

11. Additive, where the additive comprises TiO$_2$ particles supported and dispersed on a support, obtainable by the process described in claim 1.

12. Composition that comprises the additive of claim 11.

13. The composition according to claim 12, where the composition is cement or a sol-gel coating.

14. The composition according to claim 13, comprising between 0.1% and 15% by weight of the additive.

15. The composition according to claim 12, where the composition is mortar concrete, lime mortar, mixed mortar or a plaster.

16. The composition according to claim 15, comprising between 0.1% and 15% by weight of the additive over the weight of the mortar concrete, lime mortar, mixed mortar or plaster.

17. The composition according to claim 12, where the composition is paint, a coating, emulsion or protective layer.

18. The composition according to claim 17, comprising between 0.1% and 10% by weight of the additive.

19. A material with self-cleaning, biocide, deodorization and/or pollution reduction properties in the presence of air and ultraviolet light which comprises the additive of claim 11.

* * * * *